US00RE38947E

(19) United States
(12) Reissued Patent
Doyle

(10) Patent Number: US RE38,947 E
(45) Date of Reissued Patent: Jan. 24, 2006

(54) METHOD OF ENANTIOSELECTIVELY CATALYZING A REACTION

(75) Inventor: Michael P. Doyle, Glenn Dale, MD (US)

(73) Assignee: Research Corporation Technologies, Inc., Tucson, AZ (US)

(21) Appl. No.: 08/601,101

(22) Filed: Feb. 14, 1996

Related U.S. Patent Documents

Reissue of:
(64) Patent No.: 5,296,595
Issued: Mar. 22, 1994
Appl. No.: 07/950,836
Filed: Sep. 24, 1992

U.S. Applications:
(62) Division of application No. 07/502,139, filed on Mar. 29, 1990, now Pat. No. 5,175,311.

(51) Int. Cl.
*C07D 205/08* (2006.01)
*C07D 207/26* (2006.01)
*C07D 207/33* (2006.01)
*C07F 7/08* (2006.01)

(52) U.S. Cl. ..... 540/200; 502/166; 502/167; 540/362; 546/2; 548/101; 548/105; 548/403; 548/540; 549/326; 552/1; 552/8; 552/10; 556/45; 556/57; 556/137; 556/438; 556/442; 556/475; 560/17; 560/568; 560/800; 560/820; 560/910; 560/912

(58) Field of Classification Search ..... 540/200, 540/362; 502/166, 167; 546/2; 548/101, 105, 548/403, 540; 549/326; 556/45, 57, 137, 556/438, 479, 442; 552/1, 8, 10; 580/17; 568/800, 820, 910, 912
See application file for complete search history.

(56) References Cited

U.S. PATENT DOCUMENTS 4,909,911 A * 3/1990 Bear et al. ..... 204/84
5,175,311 A * 12/1992 Doyle ..... 549/302

OTHER PUBLICATIONS

Aratani, T., *Pure & App. Chem.*, 1985, 57, p. 1839.*
Aratani, T.; Yoneyoshi, Y. and Nagase, T., *Tetrahedron Lett.*, 1975, 21, 1975, p. 1707.*
Aratani, T.; Yoneyoshi, Y. and Nagase, T., *Tetrahedron Lett.*, 1982, p. 685.*
Brunner, H.; *Synthesis*, 1988, p. 645.*
Brunner, H; Kluschanzoff, H., and Wutz, K., *Bull. Soc. Chem. Belg.*, 1989, 98, p. 63.*
Dauben, W.; Hendricks, R., Kuzzio, M. and Ng, H., *Tetrahedron Lett.*, 1990, 48, p. 6969.*
Doyle, J., *Amer. Chem. Soc.*, 112, 1990, pp. 1906–1912.*
Doyle, *Chem Rev.*, 86, 1986, pp. 919–939.*
Doyle, J. *Amer, Chem. Soc.*, vol. 113, 1991, pp. 1423–1424.*
Dolye, *Tetrahedron Lett.*, 31,1990, pp. 6613 +.*
Evans, D.; Woerpel, K. and Hinman, M., *J. Amer. Chem Soc.*, 1991, 113, p. 726.*
Fritschi H.; Leutenegger, U. and Pfaltz, A., *Angew. Chem. Int. Ed. Engl.*, 1986, 11, p. 1005.*
Fritschi H.; Leutenegger, U. and Pfaltz, A., *Helvetica Chimica Acta*, 1988, 71, p. 1553.*
Kennedy, M.; McKervey, M.; Maguire, A. and Roos, G., *J. Chem. Soc. Chem. Commun.*1990, p. 361.*
Kunz, T. and Reissing, H., *Tetrahedron Lett.*, 1989, 30, p. 2079.*
Lowenthal, R.; Abiko, A. and Masamune, S., *Tetrahedron, Lett.*, 1990, 31, p. 6005.*
Maas, G., *Topics in Current Chemistry*, 1987, 137, p. 75.*
Muller, D.; Umbricht, G.; Weber, B.; Pfaltz, A., *Helvetica Chimica, Acta*, 1991, 74, p. 232.*
Nakamura, A., Konishi, A., Tatsuno, Y. and Otsuka, S., *J. Am. Chem. Soc.*, 1978, 100:11, p. 3443, and *J. Am. Chem. Soc.*, 1978, 100:11, p. 3449.*
Nozaki, H., Takaya, H., Moriuti, S. and Noyori, R., *Tetrahedron Lett.*, 1967, 24, p. 3655.*
Tomioka, K., *Synthesis*, 1989, p. 541.*
Hashimoto, S.; Watanabe, N. and Ikegami, S., *Tetrahedron Lett.*, 1990, 31, pp. 5173+.*
Aratani, T.; Yoneryoshi. And Nagase, T., *Tetrahedron Lett.*, 1977, 30, pp. 2599+.*
Doyle, M. P. et al., "Highly Selective Y–Lactone Synthesis by Intramolecular Carbenoid Carbon–Hydrogen Insertion in Rhodium(II) Carboxylate and Rhodium(II) Carboxamide Catalyzed Reactions of Diazo Esters", *Tetrahedron Letters*, 30(50), 1989, pp. 7001–7004.*
Bear, J.L. et al., "Structural, ESR, and Electrochemical Properties of Two $[RH_{2(ap)4}]_+$ Geometric Isomers (ap=–2–Anilinopyridinate), A Truse Mixed–Valent Rhodium–(I-I)–Rhodium(III) Complex", *Inorganic Chemistry*, 1987, 26, pp. 2927–2929.*
Bear, J.L. et al., "Structural, Spectroscopic, and Electrochemical Characterization of Tetrakis–$\mu$–(2–pyrrolidinonato)–dirhodium(II) and Tetrakis–$\mu$–(δ–valero–lactamato)–dirhodium(II)", *Journal of Chemical Society Dalton Transactions*, 1989, 1, pp. 93–100.*

* cited by examiner

*Primary Examiner*—Richard L. Raymond
(74) *Attorney, Agent, or Firm*—Brinks Hofer Gilson & Lione

(57) ABSTRACT

A chiral catalyst is disclosed together with methods of using it for enantioselective syntheses. The chiral catalyst includes a nucleus with two metal atoms that has four bridging ligands oriented radially to the axis of the nucleus. Each of these ligands includes a two complexing atoms each complexed to one of the metal atoms. At least one of the bridging ligands includes a chiral center which is bonded to one of the complexing atoms. Preferably, all four of the bridging ligands include a chiral center bonded to one of the complexing atoms. The catalyst of the invention has been found to be useful in catalyzing carbenoid transformation reactions such as cyclopropanation.

71 Claims, 7 Drawing Sheets

$Rh_2(4S\text{-}IPOX)_4$ $Rh_2(4S\text{-}BNOX)_4$ $Rh_2(4S\text{-}MPOX)_4$ $Rh_2(5S\text{-}MEPY)_4$, R=Me
$Rh_2(5S\text{-}IPPY)_4$, R= isopropyl $Rh_2(4R\text{-}\ IPOX)_4$ $Rh_2(4R\text{-}BNOX)_4$ $Rh_2(4R\text{-}MPOX)_4$ $Rh_2(5R\text{-}MEPY)_4$, R= Me
$Rh_2(5R\text{-}IPPY)_4$, R= isopropyl

≡

≡

METHOD OF ENANTIOSELECTIVELY CATALYZING A REACTION

Matter enclosed in heavy brackets [ ] appears in the original patent but forms no part of this reissue specification; matter printed in italics indicates the additions made by reissue.

The present application is a *reissue application of Ser. No. 07/950,836, filed Sep. 24, 1992, now U.S. Pat. No. 5,296,595, which is a* division[,] of application Ser. No. 502,139, filed [mar.] *Mar.* 29, 1990, now U.S. Pat. No. 5,175,311.

STATEMENT OF GOVERNMENT INTEREST

This invention was made with government support under Grant R15-GM-42160-01 awarded by the National Instituted of Health. The government has certain rights in the invention.

BACKGROUND OF THE INVENTION

The present invention relates to the field of catalysts. More particularly, the invention relates to catalysts which are useful in enantioselective syntheses.

In recent years, catalytic transformations of organic diazo compounds have been used as highly versatile synthetic methods. Efficient procedures for the formation of carbon-carbon bonds by cyclopropanation, dipolar addition, carbon-hydrogen insertion, aromatic substitution reactions, and ylid generation/rearrangement with allylamines, allyl sulfides, and allyl ethers have been reported.

Electrophilic metal carbenes are produced from reactions of diazo compounds with transition metal complexes that possess an open coordination site. Among the catalysts that have been employed for carbenoid transformations, rhodium (II) carboxylates, which are resistant to ligand displacement, electron transfer reactions, and olefin complexation, have been found to be effective. Also, Rhodium(II) acetamide has recently been used for trans(anti) stereoselectivity enhancement in cyclopropanation reactions.

Only a limited number of chiral catalysts for metal carbene transformations have been reported. These chiral catalysts have been successfully employed only for cyclopropane syntheses. For example, Aratani et al. have prepared chiral Schiff base complexes of copper(II) such as that with the following structure:

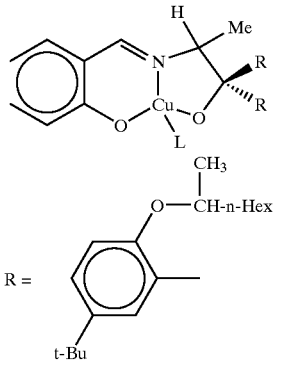

The use of this Aratani catalyst has yielded enantiomeric excesses (e.e.) as high as 90% in the synthesis of chrysanthemic acid esters. One such synthesis produces the following chrysanthemic acid ester with a 64% yield:

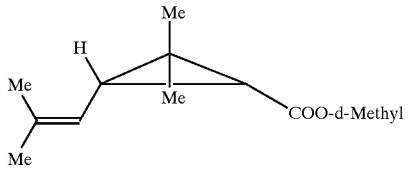

Matlin et al. reported in 1984, the use of copper(II) complexes of 3-trifluoroacetyl-(+)-camphor for the asymmetric cyclopropanation of styrene with 2-diazodimedone. Although the enantiomerically pure cyclopropane product was obtained, its reported yield was only 48%.

Other chiral copper catalysts have also been reported. In particular, chiral catalysts have been prepared from Schiff bases derived from (S)-(−)-1-phenylethylamine, from binaphthyl-o, o'-diamines, from alpha amino alcohols, from amino acids, from amino esters, from amino sugars, and from tartaric acid. However, these chiral copper catalysts have only low to moderate reported enantiomeric excesses in cyclopropanation reactions.

Nakamura and Otsuka reported in 1978 the preparation of chiral bis(1,2)-dioximato)cobalt(II) complexes derived from d-camphor having the following structure (B=pyridine):

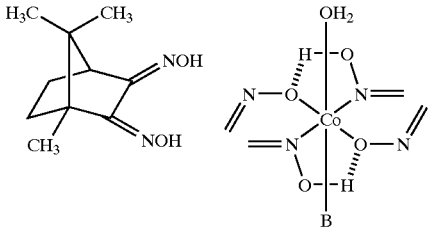

Nakamura and Otsuka also reported the use of this catalyst for cyclopropanation of conjugated dienes, styrenes, and electron-deficient alkenes that include ethyl acrylate and acrylonitrile. Vinyl ethers and mono-olefins, including cyclohexene, do not react with diazo-esters under the influence of these catalysts, thus suggesting that the intermediate metal carbene possesses nucleophilic character. Optical yields in cyclopropanation reactions catalyzed by this catalyst are moderate. Although cyclopropane yields are ordinarily high, stereoselectivities are reportedly low.

In 1989, A. Pfaltz reported the synthesis and uses of (semicorrinato)copper catalysts for enantioselective cyclopropanation reactions:

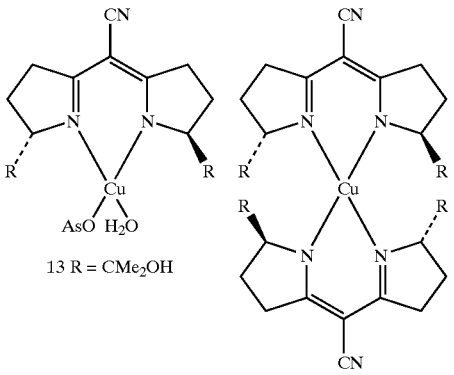

In the presence of these catalysts mono-substituted olefins react with diazo compounds to produce the corresponding cyclopropane derivatives in high optical yields. However, di- and tri-substituted olefins give low product yields.

Carbenoid insertion into the N-H bond of beta lactams has become a standard method for synthesis of carbapenam, oxapenam, carbacephem, and oxacephem systems. Rhodium(II) carboxylates have been used as the catalysts for these syntheses. An example is as follows:

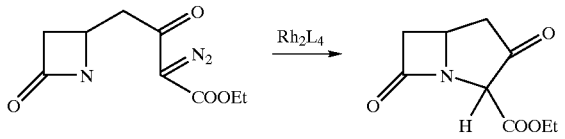

SUMMARY OF INVENTION

Briefly stated, the present invention is a chiral catalyst together with methods of using it for enantioselective syntheses. The chiral catalyst includes a nucleus with a first and second atom of the same metal aligned on an axis of the nucleus. There are four ligands which complex with the metal atoms. Each of these ligands includes a first and second complexing atom. The first complexing atom of each of the bridging ligands is complexed with the first metal atom, while the second complexing atom of each of the bridging ligands is complexed to the second metal atom. At least one of the bridging ligands includes a chiral center which is bonded to one of the complexing atoms. Preferably, all four of the bridging ligands include a chiral center bonded to one of the complexing atoms.

In accordance with one aspect of the invention, the ligand with the chiral center also has a ring including the first complexing atom and attached to the second complexing atom. In this embodiment, the chiral center is included in the ring and attached through a first bonding site to the first complexing atom and attached through a second bonding site to the ring. In this embodiment, another of the bridging ligands also has a ring including the second complexing atom and attached to the first complexing atom. A chiral center is included in the ring and is attached through a first bonding site to the second complexing atom and attached through a second bonding site to the ring. In this embodiment, the R/S configuration of the chiral center on both bridging ligands is the same. Preferably in this embodiment, the third and fourth bridging ligands also include rings and chiral centers bonded to one of the complexing atoms. Most preferably, the four bridging ligands are the same with the chiral center being bonded to the first complexing atom in two of the ligands, and bonded to the second complexing atom in the other two ligands.

In accordance with another aspect of the invention, the ligand with the chiral center also has a ring including the first complexing atom and attached to the second complexing atom. In this embodiment, there are two chiral centers on this ligand, one being attached to the first complexing atom and included in the ring, and the other being attached to the second complexing atom. The R/S configuration of both chiral centers is preferably the same.

In accordance with still another aspect of the invention, the ligand with the chiral center also includes a ring including the first complexing atom and attached to the second complexing atom. In this embodiment, the chiral center is attached through a first bonding site to the first complexing atom and attached through a second bonding site to the ring. This embodiment further includes blocking structure. Which is bonded to at least one of the bridging ligands. This blocking structure is constituted, configured and oriented so as to substantially impair approach to the second metal atom along the axis.

In accordance with yet another aspect of the invention, the first bridging ligand includes a chiral center bonded to the first complexing atom, and the second bridging ligand includes a chiral center bonded to the second complexing atom. Preferably, the third and fourth bridging ligands also include chiral centers bonded to the first and second complexing atoms respectively. In this embodiment, the R/S configuration of the chiral centers on the all four bridging ligands is preferably the same.

In accordance with still yet another aspect of the invention, the first bridging ligand includes a chiral center bonded to the first complexing atom. This embodiment further includes a blocking structure which is bonded to at least one of the bridging ligands. This blocking structure is constituted, configured and oriented so as to substantially impair approach to the second metal atom along the axis. Preferably, the second bridging ligand also includes a chiral center bonded to the first complexing atom In this preferred embodiment, the R/S configuration of the chiral centers on the first and second bridging ligands is the same.

In accordance with the method aspect of the present invention, the chiral catalysts described above are used to catalyze carbenoid transformations, such as cyclopropanation or insertion reactions, to catalyze hydrogenation, hydrosilation, and hydroboration reactions, and to form metal stabilized ylides.

The cyclopropanation aspect of the invention, includes the steps of providing an olefin and a carbene precursor. Either the olefin or the carbene precursor should be prochiral. These are reacted in the presence of the catalysts described above under such conditions sufficient to effect the cyclopropanation. The olefin and the carbene precursor may be on the same molecule to thereby effect intramolecular cyclopropanation.

The carbene insertion aspect of the invention includes the steps of providing a compound with either a carbon-hydrogen, a silicon-hydrogen, a oxygen-hydrogen, or a nitrogen-hydrogen bond and a carbene precursor. Either the compound or the carbene precursor should be prochiral. These are reacted in the presence of the catalysts described above under such conditions sufficient to effect the insertion. The carbene precursor may be on the same molecule to thereby effect intramolecular insertion.

The hydrogenation, hydroboration, and hydrosilation aspects of the invention, includes the steps of providing either a hydrogen molecule, a borohydride, or a silicon hydride, and a prochiral compound with either a carbon-carbon or a carbon-oxygen double bond. These are reacted in the presence of the catalysts described above under such conditions sufficient to effect the desired addition reaction.

The ylide formation aspect of the invention, includes the steps of providing a prochiral diazo compound with a hetero atom containing compound. This compound is reacted in the presence of the catalysts described above under such conditions sufficient to effect the metal stabilized ylide formation.

It is noted that the term "R/S configuration" as used in this specification and the appended claims is intended to have its conventional meaning, namely according to the Cahn-Ingold-Prelog convention. By this convention, the substituents bonded to the chiral center are assigned an order of precedence according to a standard set of rules based on atomic numbers. If the remaining three substituents on the chiral center are then viewed with the lowest priority substituent placed behind the chiral center, and if the direction moving from the highest to the second highest, and then to the third highest is clockwise, then the configuration is said to be R. If the direction is counterclockwise, then the configuration is said to be S.

It is also noted that, in discussing the catalysts or ligands generically, such as with FIGS. 1–4, the R and S configurations will be assigned based on the assumption that the larger group attached to the chiral center takes priority in numbering, even though this may not necessarily be the case with the specific substituents actually used.

It is further noted that the term "prochiral" is intended to refer to those compounds having an atom which by a single substitution can be converted to a chiral atom.

The chiral catalysts of the present invention are broadly applicable to carbene transformations, including cyclopropanation, insertion, and ylide generation, catalyzing the syntheses of products from these carbenoid transformations with relatively high enantioselectivity. These catalysts can generally be prepared by methods that allow a high degree of structural variation which adds to their versatility for diastereoselective and regioselective reactions. The basic design of these catalysts also allows for some degree of predictability, of the absolute configuration of the enantiomerically enriched product.

The present invention, together with its attendant objects and advantages, will be best understood with reference to the detailed description below read in conjunction with the accompanying drawings.

DETAILED DESCRIPTION OF THE PREFERRED EMBODIMENTS

FIGS. 1–4 are three-dimensional views of preferred catalyst of the present invention. As can be seen, the nucleus for the catalyst is two metal atoms. Preferably, the metal is selected from the group consisting of rhodium, ruthenium, chromium, molybdenum, tungsten, rhenium, and osmium. More preferably, the metal is selected from the group consisting of rhodium, ruthenium, and osmium but most preferably, rhodium.

Four bridging ligands are oriented radially about the axis between the two metal atoms. Each of these bridging ligands includes two complexing atoms for complexing with the metal atoms. Preferably, the ligands are carboxamides or carbamates with a nitrogen atom serving as one complexing atom, and an oxygen atom serving as the other complexing atom.

On at least one of the bridging ligands there is chiral center bonded to one of the complexing atoms, preferably to the nitrogen atom.

Because the catalyst has an active catalytic site on both sides of the catalyst, i.e. at each of the metal atoms, it important that either (1) both sides of the catalyst have a chiral center to thereby effect enantioselectivity, or (2) one side have a chiral center, and the other side have a blocking structure which would substantially impair approach to the metal atom on the other side. Otherwise, the enantioselectivity of the catalyst would be greatly reduced with the chiral side of the catalyst effecting enantioselectivity, while the "free" side of the catalyst produces a racemic mixture.

The first of these options is preferred. In other words, it is preferred to have at least one chiral center on each side of the catalyst, i.e. bonded to the complexing atom which is bonded to each of the metal atoms. This second chiral center should have the same R/S configuration as the first chiral center.

Figure 7:
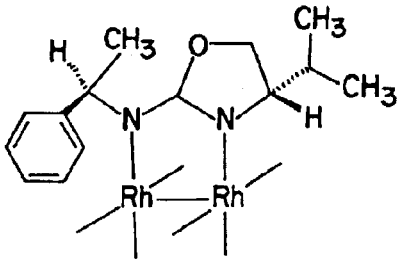
FIG. 7 is a partial three-dimensional view of a catalyst with two chiral centers on the same ligand.

Preferably, a chiral center is oriented on both sides of the catalyst by having one ligand oriented With its chiral center on one side of the catalyst and having another ligand with its chiral center on the other side of the catalyst. Alternatively, one ligand can have a chiral center bonded to both of its complexing atoms (See FIG. 7).

Even more preferably, the catalyst includes two bridging ligands with chiral centers on one side, and another two bridging ligands with chiral centers on the other side of the catalyst. These third and fourth chiral centers should have the same R/S configuration as the first and second chiral centers. Most preferably, all four bridging ligands are the same with two lined up one way, and the other two lined up the other way. This is the orientation shown in FIGS. 1–4.

Figure 8:
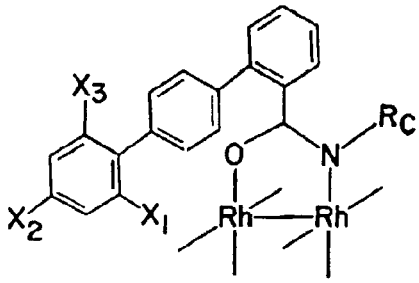
FIG. 8 is a partial three-dimensional view of a catalyst with blocking structure on one face of the nucleus.
Figure 9:
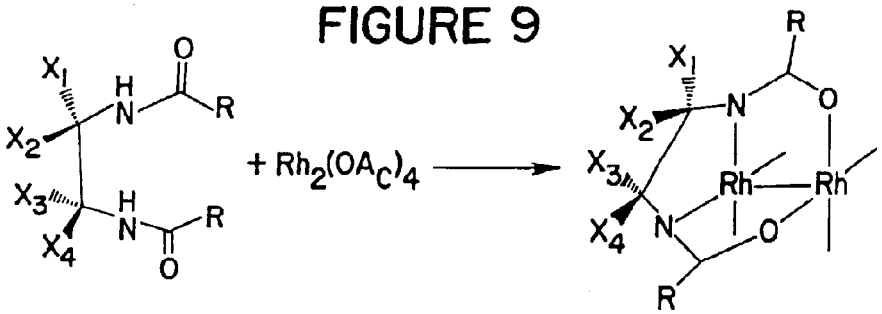
FIG. 9 shows a reaction to produce another catalyst with blocking structure on one face of the nucleus.

Although not presently preferred, the second option above, i.e. with blocking structure, as illustrated in FIGS. 8 and 9, is deemed to be within the scope of the present invention. The embodiment shown in FIG. 8 shows a chiral center $R_c$ on the right side of the catalyst with a blocking bi-phenyl structure attached to the same ligand. The substituents $X_1$, $X_2$, and $X_3$ can be selected from a wide variety including but not limited to H and alkyl groups with or without hetero atoms. As shown in FIG. 8, the bi-phenyl group in this embodiment acts to substantially impair approach to the metal atom on the left of the catalyst. By this it is meant that the carbenes and other groups to be discussed below in connection with the methods of the invention are substantially prevented from complexing with the metal on that side of the catalyst. Consequently, the enantioselectivity effected on the right side of the catalyst will predominate.

FIG. 9 shows a reaction to produce another embodiment similar to that shown in FIG. 8 wherein the left side of the catalyst includes blocking structure which substantially impairs approach to the metal atom on the left side. In particular, this catalyst is made by adding a diamide to rhodium acetate. This has the effect of placing an ethyl bridge between the two cis ligands. The substituents $X_1$, $X_2$, $X_3$ and $X_4$ can be selected from a wide variety including but not limited to H and alkyl groups with or without hetero atoms. As can be seen, the $X_1$ and $X_3$ can be selected to block the approach to the metal atom on the left side of this catalyst.

Figure 1:
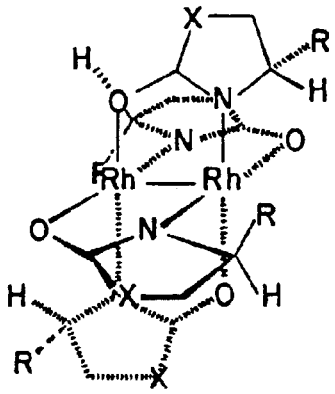
FIG. 1 is a three-dimensional view of a preferred catalyst of the present invention with a cis, S configuration.
Figure 2:
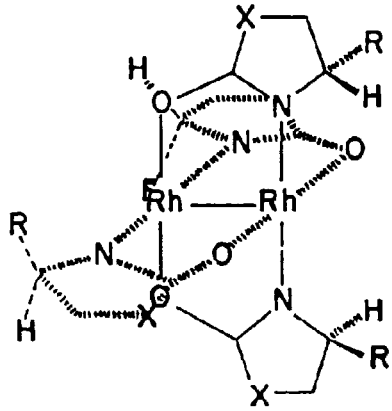
FIG. 2 is a three-dimensional view of a preferred catalyst of the present invention with a trans, S configuration.
Figure 1A:
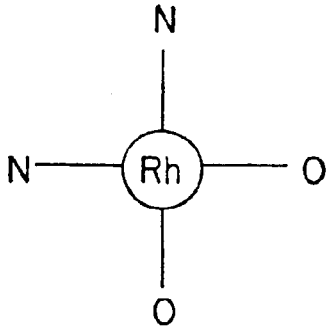
FIG. 1a is a simplified end view of the catalyst of FIG. 1 showing the cis configuration.
Figure 2A:
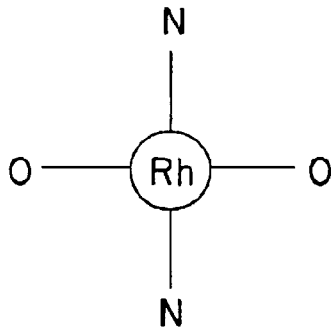
FIG. 2a is a simplified end view of the catalyst of FIG. 2 showing the trans configuration.
Figure 3:
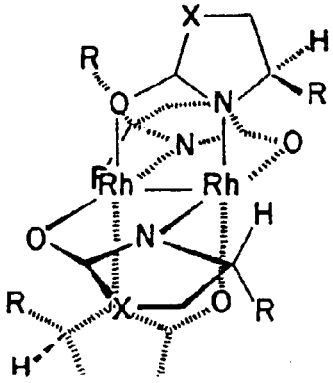
FIG. 3 is a three-dimensional view of a preferred catalyst of the present invention with a cis, R configuration.
Figure 4:
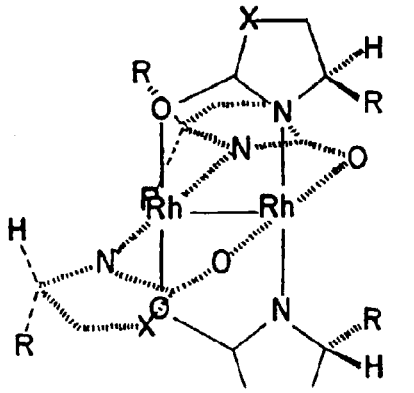
FIG. 4 is a three-dimensional view of a preferred catalyst of the present invention with a trans, R configuration.

Referring again to FIGS. 1–4, solid lines are used to depict the ligands which have the chiral center on the right, while broken lines are used to depict the ligands which have the chiral center on the left. FIGS. 1a and 2a represent simplified views from the right side of the catalysts in FIGS. 1 and 2 respectively. It can be seen, that the catalysts shown in FIGS. 1, 1a, and 3 are in a cis configuration. In other words, the bridging ligands with the chiral centers on the right are radially adjacent. The catalyst depicted in FIGS. 2, 2a, and 4 are in a trans configuration with the bridging ligands with the chiral centers on the right being radially opposite.

Experimental data has shown that the cis configuration is slightly favored over the trans. However, both the cis and trans configurations of the catalysts of the present invention have been shown to effect good enantioselectivity.

Preferably, the ligand with the chiral center comprises a ring which includes one of the complexing atoms and includes the chiral center. In this case, the chiral center has two remaining bonding sites for two different substituents, depicted as R and H in FIGS. 1–4. Because the chiral center is attached within the ring, the orientation of these two bonding sites is fixed. In particular, viewed from one end of the catalyst, the chiral center at the top will have one embodiment on the right and one substituent on the left. It is also seen that these two substituents are oriented so as to point toward any molecules approaching the metal atom of the catalyst. Consequently, and as will be described in more detail below, the two substituents on the chiral center are used to effect a facial selectivity for the catalyst.

Preferably, in this embodiment wherein the chiral center is included within a ring, one of the two remaining substituents on the chiral center will be hydrogen. When one of the substituents is hydrogen, then the other substituent can be selected from a wide variety of substituents including but not limited to alkyl groups with or without hetero atoms. When one substituent is hydrogen, then the other substituent can also be a halide. Most preferably, one of the substituents is hydrogen and the other is selected from the group consisting of methyl, ethyl, isopropyl, benzyl, carbonyl, carboxylates, and carboxamides.

*The bridging ligands can be selected from the group consisting of: Oxazolidinones, Pyrrolidinones, *B-lactams, *Y-lactams, *S-lactams, and their analogs wherein S replaces O as the complexing atom. The bridging ligands can also be selected from the group consisting of* (4*S*) *isopropyl oxazolidinone*, (4*S*) *benzyl oxazolidinone,* (4*S*) *methyl oxazolidinone,* (5*S*) *methyl* 2*-pyrrolidinone-*5*-carboxylate,*(5*S*) *isopropyl* 2*-pyrrolidinone-*5*-carboxylate.*

FIGS. 5a–d show currently preferred cyclic bridging ligands in the S configuration.

Figure 5A:
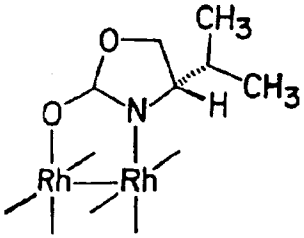
FIGS. 5a–d show the structure of the preferred cyclic chiral ligands with an S configuration.

FIG. 5a shows the ligand (4S)-isopropyloxazolidinone which has been assigned the designation 4S-IPOX.

Figure 5B:
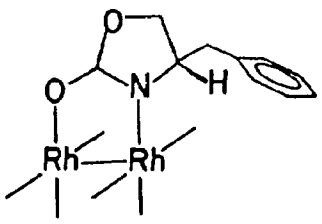

FIG. 5b shows the ligand (4S)-benzyloxazolidinone which has been assigned the designation 4S-BNOX.

Figure 5C:
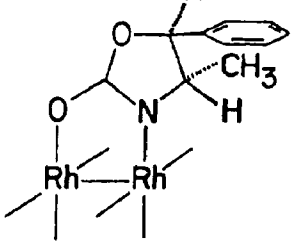

FIG. 5c shows the ligand (4S)-methyl-5-phenyloxazolidinone which has been assigned the designation 4S-MPOX.

Figure 5D:
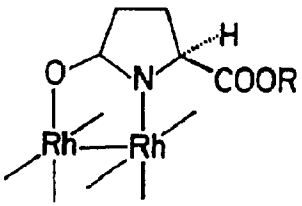

FIG. 5d shows the ligand (5S)-methyl-2-pyrrolidinone-5-carboxylate where R=methyl, and (5S)-isopropyl-2-pyrrolidinone-5-carboxylate where R=isopropyl. There have been assigned the designations S-MEPY and 5S-IPPY, respectively.

FIGS. 6a–6d show the same ligands in the R configuration.

Figure 10:
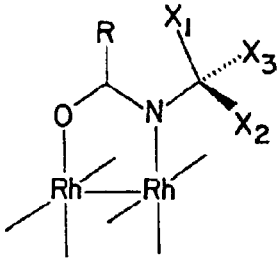
FIG. 10 is a partial three-dimensional view of a catalyst where the chiral center is not bound in a ring.
Figure 10:
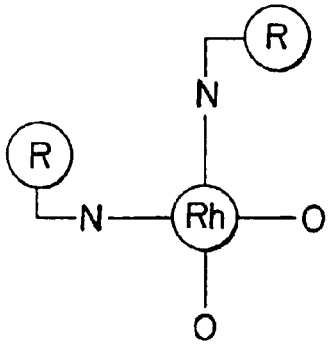

Although preferred, it is not necessary that the chiral centers be included in a ring. FIG. 10 is a view similar to those above wherein the ligand is a N-substituted amide with a chiral carbon bonded to one of the nitrogen atoms. The substituents $X_1$, $X_2$, and $X_3$ on the chiral center can be varied widely. Naturally, because the carbon is a chiral center, it is required that all three of these substituents differ from one another. As will be explained below, it is important that one of the substituents be significantly larger than one of the other substituents.

Preferably, one of the substituents on the catalyst shown in FIG. 10 will be hydrogen. The other substituents can be selected from a wide variety of groups including but not limited to alkyl groups with or without hetero atoms. Most preferably, one of the substituents is hydrogen and the other other two are independently selected from the group consisting of methyl, ethyl, isopropyl, benzyl, carbonyl, and carboxylate. These substituents are believed to align themselves so as to provide an orientation of minimum total energy and thereby influence the approach of reactant molecules towards the metal center.

While not wishing to bound by any particular theory, it is currently believed that the proposed mechanism illustrated in FIGS. 11, 12a–b, 13a–b, and 14 explains the remarkable enantioselectivity achieved by the catalyst of the present invention.

Figure 11:
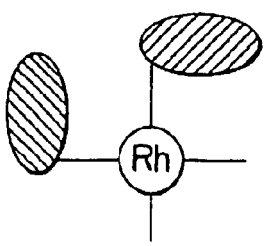
FIG. 11 illustrates the proposed influence of the chiral ligands to direct selective attachment of reactive intermediates in the catalysts of the present invention.
Figure 11:
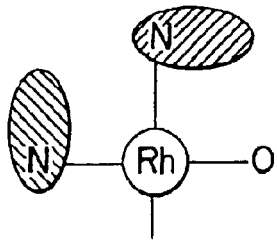

FIG. 11 is used to illustrate the spatial implications of the chiral center bonded to the complexing atom, which in this case is nitrogen. Because one of the out-facing substituents on the chiral center takes up more volume than the other out-facing substituent, there is created a sterically preferred orientation for a carbene intermediate complexed to the metal atom.

Figure 12A:
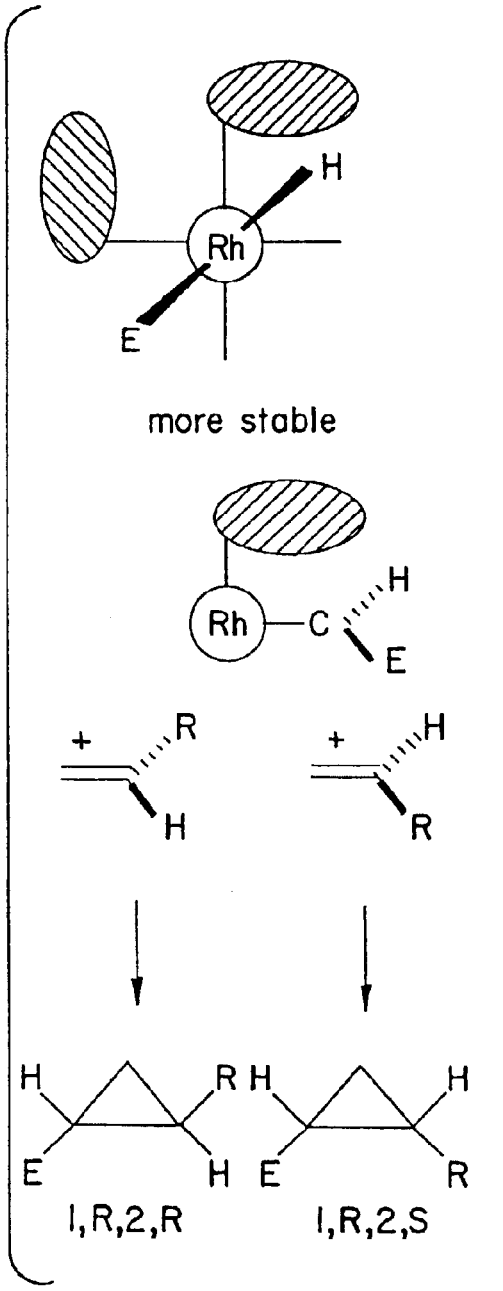
FIGS. 12a, 12b, 13a and 13b illustrate the proposed mechanism as it pertains to cyclopropanation.
Figure 12B:
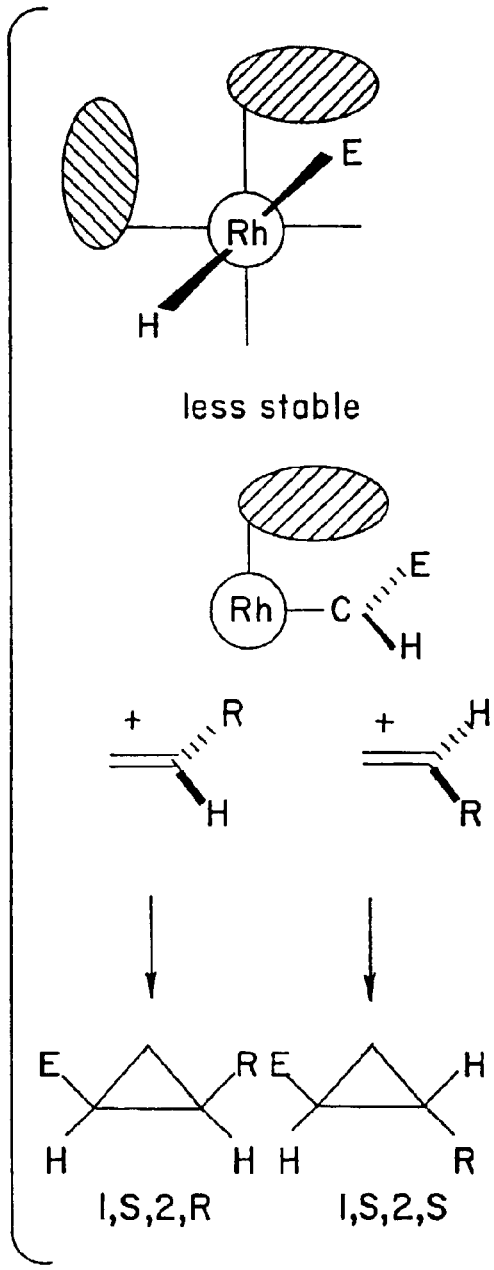

FIGS. 12a and 12b show how the sterically preferred orientation is achieved. The first line of these FIGURES shown the two different orientations of a carbene precursor to the metal atoms. The carbene precursor has an ester on one side and a hydrogen on the other. Because of steric hindrance, the orientation shown in FIG. 12b is less stable than that shown in FIG. 12a.

The second line of FIGS. 12a and 12b is a view showing the restricted access of the olefin substrate to the carbene. The third line of the FIGURES shows the four different orientations of the substrate as it approaches the carbene The fourth line of the FIGURES shows the four different enantiomers produced Because, the orientation of the carbene in FIG. 12a is more stable, more of the (1R,2R)- and (1R,2S)-enantiomers for the trans and cis disubstituted cyclopropanes will be produced, thereby effecting the enantioselectivity observed.

Figure 13A:
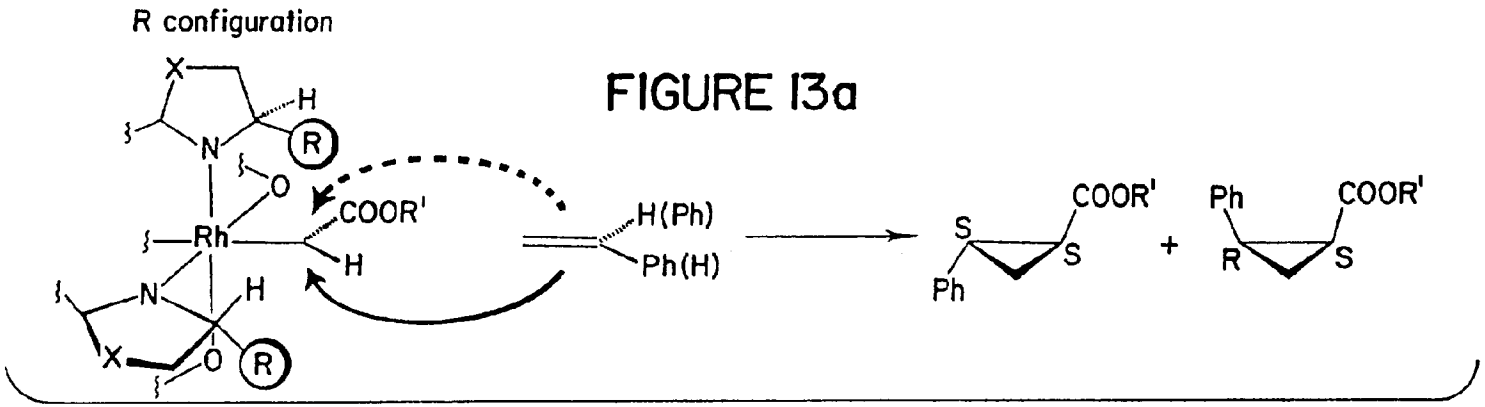
Figure 13B:
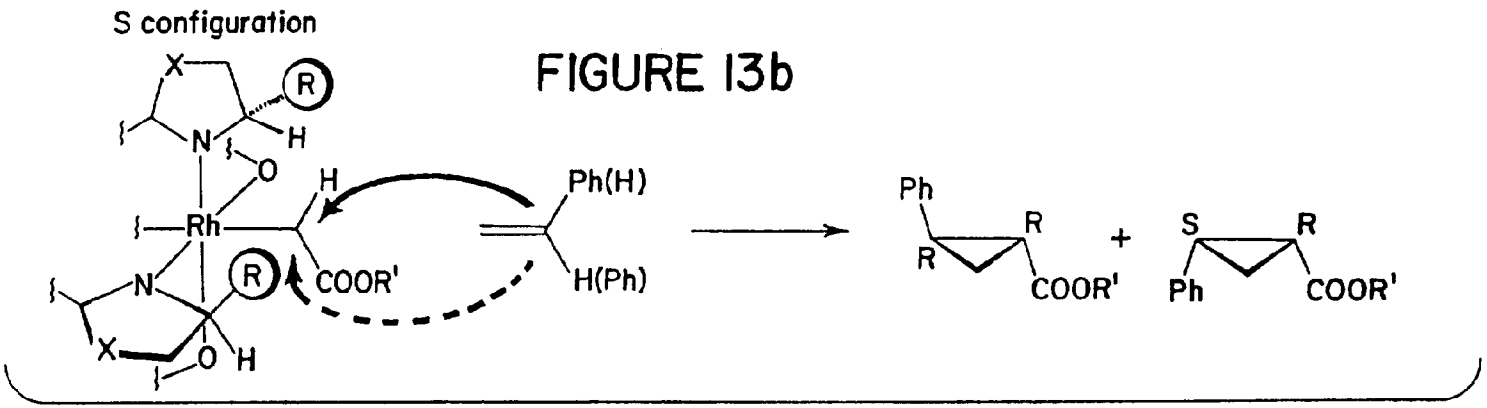

FIG. 13a and 13b further illustrates this proposed mechanism, particularly for cyclopropanation. As can be seen in FIG. 13a which shows the R configuration at the chiral centers, the approach of the olefin substrate from the top (as drawn) is sterically disfavored by the presence of the R configuration with the larger group on the two chiral centers on the right side of the catalyst. Approach from the bottom is favored with the R configuration, thereby favoring the cyclopropane enantiomers shown.

In contrast, the S configuration shown in FIG. 13b favors approach of the olefin from the top.

Figure 14:
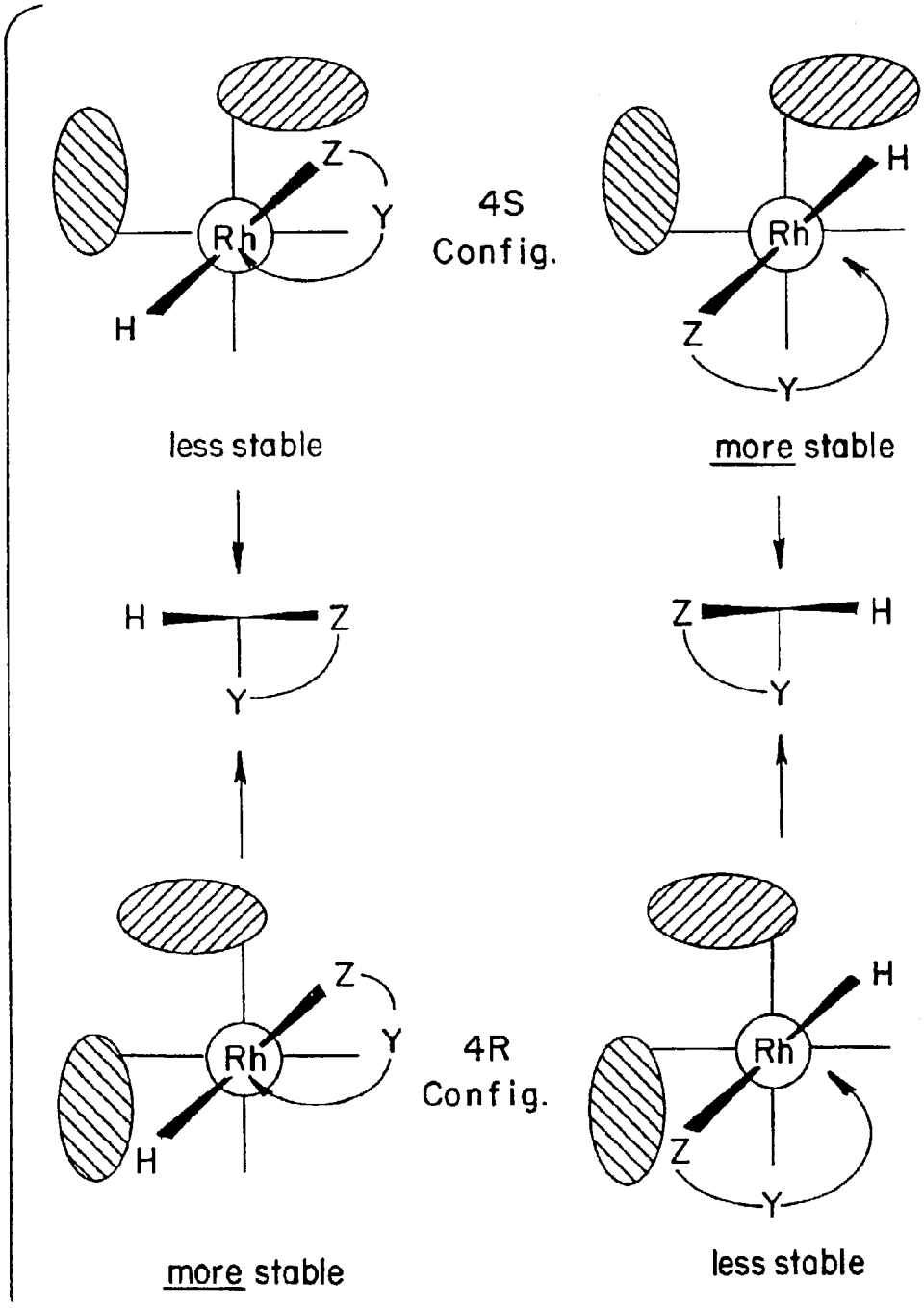
FIG. 14 illustrates the proposed mechanism as it pertains to intramolecular cyclizations.

FIG. 14 is a simplified illustration to demonstrate the proposed mechanism as it relates to intramolecular cyclizations. The top of FIG. 14 shows a catalyst with the chiral centers in the S configuration As can be seen, the orientation and approach shown on the top right is sterically more stable than that shown on the top left. Consequently, the enantiomer shown at the right is favored when using the S configuration of the catalyst.

Figure 15:
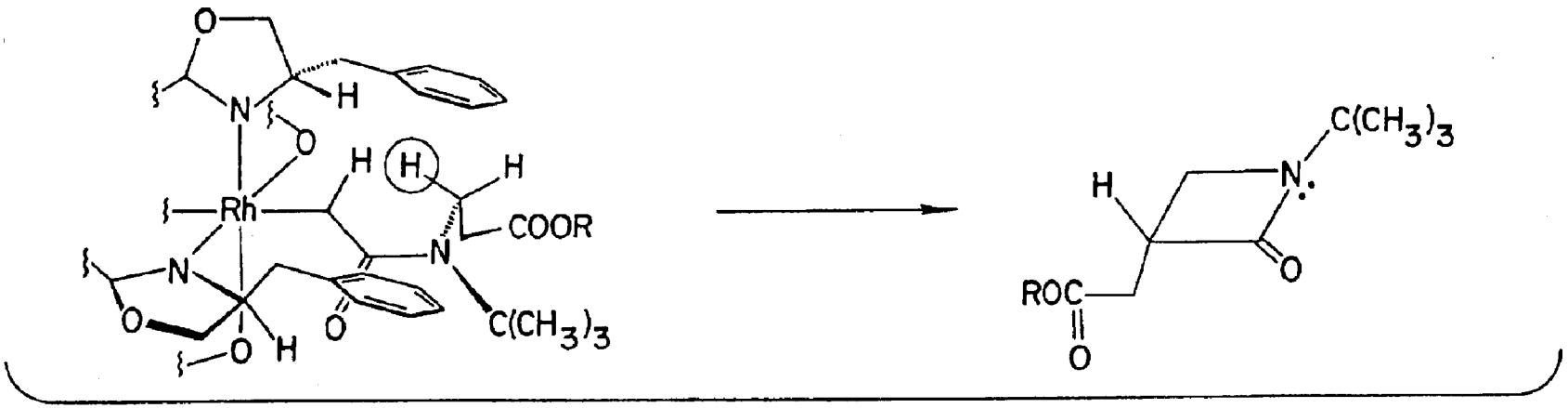
FIG. 15 illustrates the synthesis of β-lactam compounds with the catalyst of the present invention.

Conversely, the bottom of FIG. 14 shows a catalyst in the R configuration. This configuration favors the orientation shown at the bottom left. Consequently, the enantiomer shown at the left is favored when using the R configuration of the catalyst FIG. 15 shows the approach of the substrate in the synthesis of B*-lactam. As can be seen, approach of the reacting carbon-hydrogen bond occurs preferentially from in back of the carbene carbon to avoid interaction with the benzylic substituent of the ligand in front-side approach.

It should be borne in mind that, although the above-described mechanism accurately predicts the high degree of enantioselectivity observed in the catalysts of the present invention, the mechanism is at present only a theory. As such, the proposed mechanism should in no way limit the scope of the present invention as defined by the appended claims.

Consistent with observed data and consistent with the proposed mechanism described above, the size of the substituents attached to the chiral centers is important to the enantioselectivity of the catalysts of the present invention. More particularly, the relative volume of the substituents attached to the chiral centers is believed to be important in producing the steric effects by which the catalysts are thought to achieve enantioselectivity.

The following are calculations and comparisons of group volumes of groups useful as substituents on the chiral centers:

Volume of H = 2.30 $\pi$ Å$^3$

Ratio of volumes

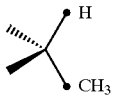

$$\frac{H}{CH_3} = \frac{2.3\,\pi}{10.7\,\pi} = 0.215$$

C—H bond length = 1.1Å

H van der Waals' radius = 1.2Å

C—C bond length = 1.5Å

$H_3C$ van der Waals' radius = 2.0Å

Volume of sphere = $\frac{4}{3}\pi r^3$

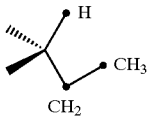

Volume of cylinder = $\pi r^2$ (length)

-continued

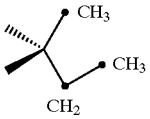

r = van der waals' radius = 2.0Å

Volume $CH_3$ = 10.7 $\pi$ Å$^3$ r = van der Waals' radius = 2.0Å

1 = bond length + van der Waals' radius = 3.5Å

Volume $CH_2CH_3$ = 14 $\pi$ Å$^3$ $$\text{Ratio of Volumes, } \frac{CH_3}{CH_2CH_3} = \frac{10.7\,\pi}{14\,\pi} = 0.76$$

Ethyl versus n-Propyl:

| | $(CH_3CH_2)$ | $(CH_3CH_2CH_2)$ |
|---|---|---|
| Radius | 2.0Å | 2.0Å |
| length (l) | 3.5Å | 2 X bond length + van der Waals' radius = 5.0Å |
| volume | 14 $\pi$Å$^3$ | 20 $\pi$Å$^3$ |

$$\text{ratio of volumes } \frac{CH_3CH_2}{CH_3CH_2CH_2} = \frac{14\,\pi}{20\,\pi} = 0.70$$

n-Propyl Versus n-Butyl:

| | $(CH_3CH_2CH_2)$ | $(CH_3CH_2CH_2CH_2)$ |
|---|---|---|
| radius | 2.0Å | 2.0Å |
| length (l) | 5.0Å | 6.5Å |
| volume | 20 $\pi$Å$^3$ | 26 $\pi$Å$^3$ |

$$\text{ratio of volumes} = \frac{20\,\pi}{26\pi} = 0.77$$

n-Butyl versus tert-Butyl

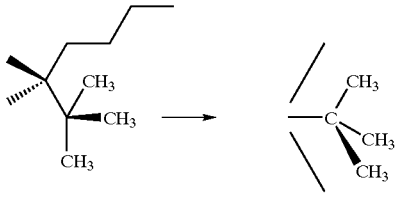

van de Waal's radii CONE

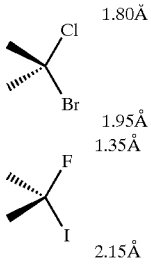

$$\text{volume ratio } \frac{Cl}{Br} = \frac{7.78\,\pi}{9.89\,\pi} = 0.79$$

$$\text{volume ratio } \frac{F}{I} = \frac{3.28\,\pi}{13.25\,\pi} = 0.25$$

Based on these volume calculations and comparisons and on observed data, it is preferred that the ratio of the volume of the smaller substituent to the volume of the larger substituent be less than about 0.8, and more preferably, less than about 0.5. When the chiral center is included in a ring, then there are only two substituents that figure into this ratio. When the chiral center is not included in a ring, the two substituents to look at are the largest and the smallest by volume (e.g. H and phenyl in the following chiral center):

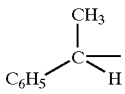

The catalysts of the present invention can be prepared by various means. Most preferably, the rhodium-based catalysts of the invention are prepared by substitution reactions with rhodium(II) acetate. Examples 1–6 below provide further details concerning the preparing of the catalyst. In an especially preferred method of preparing the catalysts of the invention, the catalyst is not isolated from the solution it is prepared in, but rather the solution is used directly in the catalyzed syntheses (See Example 6 below).

The primary class of reactions catalyzed by the catalysts of the present invention are generally known as carbenoid transformations. In this class of reactions, a carbene precursor is used to generate a carbene at the coordination sites on either of the metal atoms. Preferably, the carbene precursor is a diazo compound wherein the carbene is generated by the removal of $N_2$ as nitrogen gas from the solution. More preferably, the carbene precursor is a diazo carbonyl compound. Most preferably, the carbene precursor is a diazo compound selected from the group consisting of ethyl diazo acetate, t-butyl diazoacetate, 2,3,4-trimethyl-3-pentyl diazoacetate, menthyl diazoacetate, and 2,5-dimethyl-4-hexen-2-yl diazoacetate, and 3-(diazoacetyl)amino propionate, and diazoacetyl)amino acetate.

The carbene precursor formed on the coordination site of the metal atom can then be added to a substrate. In the cyclopropanation method of the invention, the substrate is an olefin and the carbene adds across the double bond to produce cyclopropane. An example of this reaction is as follows:

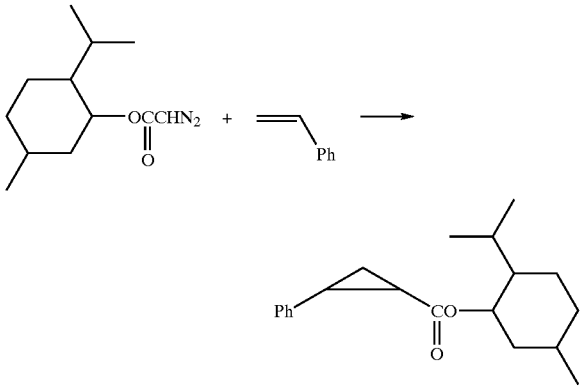

In order to benefit from the enantioselectivity of the present catalysts, either the olefin or the carbene precursor need to be prochiral, i.e. the cyclopropanation should lead to a chiral molecule.

In some reactions, the carbene precursor and the substrate can be on the same molecule, thereby effecting intramolecular cyclopropanation. An example is as follows:

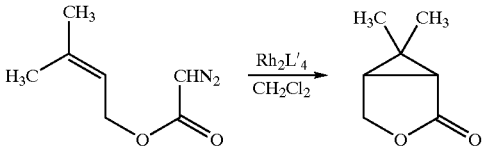

Preferably, the olefin used in the cyclopropanation reaction is selected from the group consisting of ethyl vinyl ether, styrene, 3,3-dimethyl-1-butene, 1,1,1-trichloro-4-methyl-3-pentene, and 2,5-dimethyl-2,4-hexadiene. Also, the carbene precursor is preferably a diazo carbonyl compound. More preferably, the carbene precursor is a diazo compound selected from the group consisting of ethyl diazoacetate, t-butyl diazoacetate, 2,3,4-trimethyl-3-pentyl diazoacetate, menthyl diazoacetate, and 2,5-dimethyl-4-hexen-2-yl diazoacetate.

Another type of carbenoid transformation reaction which in enantioselectively catalyzed by the catalysts of the present invention is generally known as C—H insertion reactions. In these reactions, the carbene is added across a C—H bond. As with the cyclopropanation, the carbene precursor and the C—H bond can be on the same molecule, to thereby effect an intramolecular cyclization reaction. Important examples of such reactions are the B*-lactam synthesis shown in FIG. 15 and the preparation of 4-(2-methyl-1-propenyl) 5,5-dimethyl-Y*-butyrolactone:

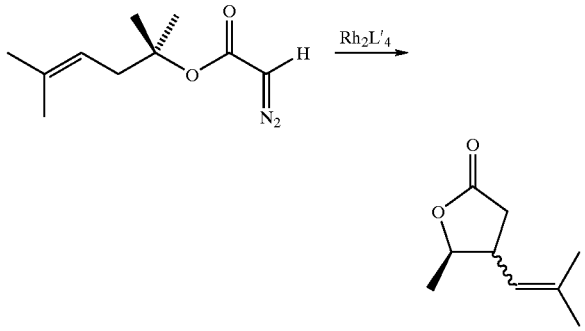

In this C—H insertion, the compound is preferably selected from the group consisting of 3-(N-diazoacetyl) aminopropionate, 2,5-dimethyl-4-buten-1-yl diazoacetate, (N-(diazoacetylamino)acetate, n-octyl diazoacetate, and N-(1-butyl)diazoacetamide. Also, the carbene precursor is preferably a diazo carbonyl compound, most preferably a diazo compound selected from the group consisting of ethyl diazoacetate, t-butyl diazoacetate, and menthyl diazoacetate. In some syntheses it is preferred for the carbene precursor to be on the same compound with the carbon-hydrogen bond, to thereby effect an intramolecular insertion.

This same insertion mechanism can be applied to insert a carbene across an O—H, N—H and Si—H, and S—H bond.

In the O—H insertion reaction it is preferred that the O—H containing compound be selected from the group consisting of cis-1,2-cyclohexanediol, 1-phenylethyanol, menthol, and 2-butanol. As above, it is preferred that the carbene precursor be a diazo carbonyl. Most preferably the carbene precursor is a diazo compound selected from the group consisting of ethyl diazoacetate, t-butyl diazoacetate, menthyl diazoacetate, and 3-diazo-2-butanone. Also, the carbene precursor can be located on the same compound with the O—H bond to effect an intramolecular insertion.

In the N—H insertion reaction, it is preferred that the N—H containing compound be selected from the group consisting of N-(1-phenylethyl)acetamide, N-(2-butyl) acetamide, and 3-acetyl-B*-lactam. The carbene precursor is preferably a diazo carbonyl compound, most preferably selected from the group consisting of ethyl diazoacetate, t-butyl diazoacetate, methyl diazoacetate, and 3-diazo-2-butanone. As above, the carbene precursor can be located on the same compound with the O—H bond to effect an intramolecular insertion.

In the Si—H and S—H insertion reaction, the carbene precursor is preferably a diazo carbonyl compound, most preferably, a diazo compound selected from the group consisting of ethyl diazo acetate, t-butyl diazoacetate, methyl diazoacetate, and 3-diazo-2-butanone. As with the other insertion reactions, the carbene precursor can be located on the same compound with the S—H bond to thereby effect an intramolecular insertion.

The catalysts of the present invention are also useful in the enantioselective formation of metal stabilized ylides. To do so, a prochiral diazo compound and a heteroatom containing compound are reacted with the catalyst of the present invention. The metal stabilized ylide is then believed to undergo reactions characteristic of these ylides including, but not limited to, [2,3-]-sigmatropic rearrangements and [1,2]-insertion reactions (Stevens rearrangement).

The catalysts of the present invention are also useful in enantioselective hydrogenation reactions. In these reactions, a hydrogen source is reacted with a compound having a C—C double bond or a C—O double bond in the presence of the catalyst of thereby add hydrogen across the double bond. The hydrogen source can be molecular hydrogen and silane. Example of such reactions are as follows:

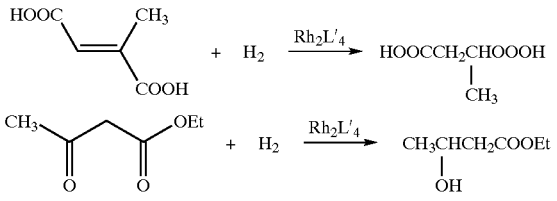

The catalysts of the present invention are also useful in enantioselective hydrosilation and hydroboration reactions. In these reactions, a compound with a C—C or a C—O double bond is reacted with a silicon or a boron hydride in the presence of the catalyst. The following are examples of this type of reaction:

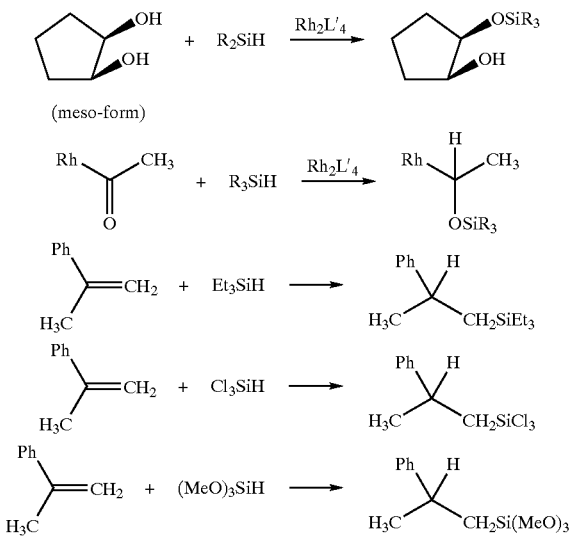

EXAMPLES

The following examples are provided by way of explanation and illustration. As such, these examples are not to be viewed as limiting the scope of the invention as defined by the appended claims.

EXAMPLE 1

Preparation of catalyst Dirhodium(II) Tetrakis[(S)-(−)-4-benzyl-2-oxazolidinone](Rh$_2$[4S-BNOX]$_4$) (See FIG. 5b)

Rhodium(II) acetate (0.497 g, 1.12 mmol), prepared from rhodium trichloride according to the literature procedure (G. A. Rampel et al., Inorganic Synthesis. 13, 90 (1972)), and (S)-(−)-4-benzyl-2-oxazolidinone (2.40 g, 13.6 mmol) obtained from the Aldrich Chemical Company (29,464-0), in 50 mL of anhydrous chlorobenzene was refluxed under nitrogen in a Soxhlet extraction apparatus. The thimble was charged with a 3:1 mixture of sodium carbonate and sand which had been dried at 110° C. for 3 h, and a new thimble containing the sodium carbonate-sand mixture was introduced after refluxing for 24 h. After 49 h, as evidenced by HPLC analysis on a u-Bondapak-CN column, the dirhodium composite was >99% Rh$_2$(4S-BNOX)$_4$. Chlorobenzene was removed by distillation, and the resulting purple solid was chromatographed on a silica gel column using acetonitrile hexane (3:97 to 30:70) to separate the excess oxazolidinone and decomposed dirhodium compounds. Elemental analysis confirmed the product formulation as Rh$_2$(BNOX)$_4$.

EXAMPLE 2

Figure 6A:
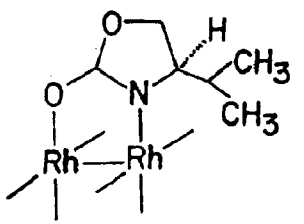
FIGS. 6a–d show the structure of the preferred cyclic chiral ligands with an R configuration
Figure 6B:
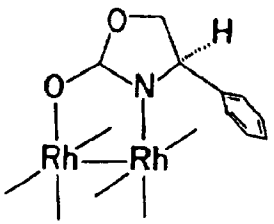
Figure 6C:
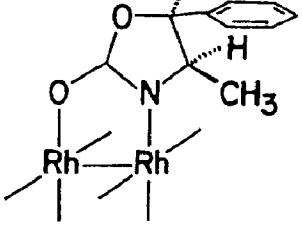
Figure 6D:
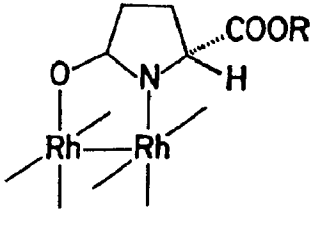

Preparation of catalyst Dirhodium(II) Tetrakis [(R)-(+)-4-benzyl-2-oxazolidinone](Rh$_2$[4R-BNOX]$_4$) (See FIG. 6b)

Rhodium(II) acetate (0.218g, 0.493 mmol) and (R)-(+)-4-benzyl-2-oxazolidinone (1.770 g, 10.0 mmol), from Fluka Chemical Company, in 50 mL of anhydrous chlorobenzene was refluxed under nitrogen for 39 h in a Soxhlet extraction apparatus according to the procedure in the previous example. Chromatographic separation of the purple solid, obtained after distillation of chlorobenzene, on a silica gel column, as previously described, yielded fractions that by HPLC analyses were >99.5% Rh$_2$(4R-BNOX)$_4$.

EXAMPLE 3

Preparation of catalyst dirhodium(II) tetrakis[(4S)-(−)-4-isopropyl-2-oxazolidinone](Rh$_2$[4R-IPOX]$_4$) (See FIG. 6a)

The subject catalyst was made in a procedure similar to that in Example 2.

EXAMPLE 4

Preparation of catalyst dirhodium(II) tetrakis[(4R, 5S)-(+)-4-methyl-5-phenyl-2-oxazolidinone]. (Rh$_2$[4R-MPOX]$_4$) (See FIG. 6c)

The subject catalyst was made in a procedure similar to that in Example 2.

EXAMPLE 5

Preparation of catalyst Dirhodium(II) Tetrakis [Isopropyl (S)-(−)-2-pyrrolidone-5-carboxylate](Rh$_2$[5S-IPPY]$_4$) (See FIG. 5d)

Rhodium(II) acetate (0.112 g, 0.250 mmol) and isopropyl (S)-(−)-2-pyrrolidone-5-carboxylate (1.20 g, 7.02 mmol), obtained by esterification of commercially available (S)-(−)-2-pyrrolidone-5-carboxylic acid (Aldrich Chemical Company), in 25 mL of anhydrous chlorobenzene was refluxed under nitrogen for 22 h in a Soxhlet extraction apparatus according to the procedure in the previous example. Chromatographic separation through a Bondapak-CN column using methanol-water (80:20) as the eluent yielded fractions that by HPLC analyses were >99% Rh$_2$(5S-IPPY)$_4$.

EXAMPLE 6

In Situ Catalyst Preparation and cyclopropanation

Rhodium(II) acetate (0.103g, 0.232 mmol) and methyl (S)-(−)-2-pyrrolidone-5-carboxylate (0.628 g, 4.20 mmol), obtained by esterification of (S)-(−)-2-pyrrolidone-5-carboxylic acid, in 25 mL of anhydrous chlorobenzene (or toluene) was refluxed under nitrogen for 7.5 h (17 h in toluene) in a Soxhlet extraction apparatus. Aliquots were removed at regular intervals (2–3 h) to evaluate the enantioselectivity of the mixture towards cyclopropanation of styrene with 1-menthyl diazoacetate [(1R,2S,5R)-2-isopropyl-5-methylcyclohexyl diazoacetate]. The reflux time for optimum enantioselective cyclopropanation was repeated, and the resulting solution was employed as the catalyst solution for applications. Similar procedures were employed with 1-menthyl (S)-(−)-2-pyrrolidone-5-carboxylate, d-menthyl (S)-(−)-2-pyrrolidone-5-carboxylate, 1-phenethyl (S)-(−)-pyrrolidinone-5-carboxylate, and the amide derivative of (S)-(−)-2-pyrrolidone-5-carboxylic acid derived from pyrrolidine. HPLC analyses on a u-Bondapak-CN column were used to monitor the extent of ligand substitution on rhodium(II) acetate.

EXAMPLE 7

Preparation of Ethyl 2-Phenylcyclopropanecarboxylate

To a mixture of styrene (2.15g, 20.7 mmol) and $Rh_2$(4S-BNOX)$_4$ (0.0113 g, 0.0131 mmol) in 5.0 mL of anhydrous dichloromethane was added, by syringe at room temperature, ethyl diazoacetate (0298 g, 2.62 mmol) in 3.0 mL of dichloromethane under nitrogen and at an addition rate of 0.8 mL/h (syringe pump). After addition was complete, the dichloromethane solution was passed through a plug of neutral alumina to separate the catalyst, and solvent and excess styrene were removed under reduced pressure Gas chromatographic separation of the trans-isomer produced a material whose specific rotation was −6.4° which corresponded to an enantiomeric excess of the ethyl (1R, 2R)-2-phenylcyclopropanecarboxylate. Conversion of the ethyl esters to the 1-menthyl esters by base hydrolysis, acid chloride formation, and esterification with (−)-menthol provided a gas chromatographically separable mixture that showed 25% enantiomeric excess for the (1R,2R)-enantiomer of the trans-2-phenylcyclopropanecarboxylate.

EXAMPLE 8

Preparation of 1-Menthyl 2-Phenylcyclopropanecarboxylate

To a mixture of styrene (1.063 g, 10.2 mmol) and $Rh_2$(4R-BNOX)$_4$ (0.0050 g, 0.0058 mmol) in 3.0 mL of refluxing anhydrous dichloromethane was added, by syringe at room temperature, 1-menthyl diazoacetate (0.109 g, 0.485 mmol) in 3.0 mL of dichloromethane under nitrogen &nd at an addition rate of 0.8 mL/h (syringe pump). After addition was complete, the dichloromethane solution was passed through a plug of neutral alumina, and solvent was removed under reduced pressure. The residue was analyzed by capillary gas chromatography (SPB-5 column) for diastereomeric separation and enantiomeric purity. Similar procedures were followed for the cyclopropanation of 3,3-dimethyl-1-butene, ethyl vinyl ether, and dihydropyran.

EXAMPLE 9

Cyclopropanation Reactions With Styrene and Menthyl Diazoacetate Compared

The procedure of Example 8 was repeated for 1- and d-menthyl diazoacetate With different preferred catalysts of the present invention. The results of the syntheses are listed in Table 1 below along with the reported values for the Aratani copper catalyst (ACu), and the Pfaltz copper catalyst (PCu), and observed values for $Rh_2(OAc)_4$:

TABLE 1

| CATALYST | MDA | TRANS:CIS | % EE TRANS | % EE CIS |
|---|---|---|---|---|
| PCu | 1 | 85:15 | 91 (1S, 2S) | 90 (1S, 2R) |
| PCu | d | 82:18 | 97 (1S, 2S) | 95 (1S, 2R) |
| (R)-ACu | 1 | 86:14 | 69 (1S, 2S) | 54 (1S, 2R) |
| (S)-ACu | 1 | 82:18 | 81 (1R, 2R) | 78 (1R, 2S) |
| $Rh_2(OAc)_4$ | 1 | 68:32 | 6 (1R, 2R) | 12 (1R, 2S) |
| $Rh_2$(4S-IPOX)$_4$ | 1 | 69:31 | 42 (1R, 2R) | 55 (1R, 2S) |
| $Rh_2$(4S-IPOX)$_4$ | d | 75:25 | 0 (1R, 2R) | 10 (1R, 2S) |
| $Rh_2$(4S-BNOX)$^4$ | 1 | 65:35 | 30 (1R, 2R) | 58 (1R, 2S) |
| $Rh_2$(4S-BNOX)$_4$ | d | 57:43 | 2 (1R, 2R) | 6 (1R, 2S) |
| $Rh_2$(4R-BNOX)$_4$ | 1 | 70:30 | 8 (1S, 2S) | 8 (1S, 2S) |
| $Rh_2$(4R-BNOX)$_4$ | d | 74:26 | 30 (1S, 2S) | 68 (1S, 2R) |
| $Rh_2$(4R-MPOX)$_4$ | 1 | 71:29 | 4 (1R, 2R) | 4 (1R, 2S) |
| $Rh_2$(4R-MPOX)$_4$ | d | 77:23 | 23 (1S, 2S) | 20 (1S, 2R) |
| $Rh_2$(4S-IPOX)$_4$ | 1 | 69:31 | 42 (1R, 2R) | 55 (1R, 2S) |
| $Rh_2$(4S-BNOX)$_4$ | 1 | 65:35 | 30 (1R, 2R) | 58 (1R, 2S) |
| $Rh_2$(4R-MPOX)$_4$ | 1 | 71:29 | 4 (1R, 2R) | 4 (1R, 2S) |
| $Rh_2$(5S-MEPY)$_4$ | 1 | 78:22 | 55 (1S, 2S) | 66 (1S, 2R) |

EXAMPLE 10 cyclopropanation Reactions With 1-Menthyl Diazoacetate and Different Olefins Compared The procedure of Example 8 was repeated for four different olefins. The results are presented in Table 2 below:

TABLE 2

| OLEFIN | CATALYST | TRANS:CIS | % EE TRANS | % EE CIS |
|---|---|---|---|---|
| Ethyl Vinyl Ether | $Rh_2$(4S-IPOX)$_4$ | 63:37 | 23 | 25 |
| Styrene | $Rh_2$(4S-IPOX)$_4$ | 69:31 | 42 | 55 |
| 3,3-dimethyl-1-butene | $Rh_2$(4S-IPOX)$_4$ | 83:17 | 54 | 64 |
| 2,5-dimethyl-2,4-hexadiene (EDA) | $Rh_2$(4S-IPOX)$_4$ | 62:38 | 47 | 14 |
| 2,5-dimethyl-2,4-hexadiene (EDA) | $Rh_2$(4R-MPOX)$_4$ | 17:83 | 12 | 10 |

EXAMPLE 11

(+)-(1S,2R)-cis-6,6-dimethyl-3-oxabicyclo[3.1.0] hexan-2-one by Intramolecular Cyclopropanation To 0.2 ml of in situ generated $Rh_2$(2S-MEPY)$_4$ and 25 mL of refluxing anhydrous dichloromethane was added 3-methyl-2-butene-1-yl diazoacetate (300 mg, 2.0 mmol) in 5.0 mL of dichloromethane by syringe pump over a period of 8 h. Typical workup of the solution and evaporation of solvent gave a residue identified as the title compound (83% purity) having a specific rotation of +56.8° (c=4.6 of $CHCl_3$) that after chromatographic purification yielded the title compound with an optical rotation corresponding to a minimum enantiomeric excess of 87%.

The results of this synthesis performed with the 4S-IPOX, 4S-BNOX, 4R-MPOX, and 5S-MEPY catalysts are compared in the Table 3 below.

TABLE 3

| CATALYST | $[\alpha]_D$ | PURITY, % | % EE |
|---|---|---|---|
| $Rh_2(4S\text{-}IPOX)_4$ | −37 | 94 | 44 |
| $Rh_2(4S\text{-}BNOX)_4$ | −48 | 95 | 57 |
| $Rh_2(4R\text{-}MPOX)_4$ | +39 | 85 | 51 |
| $Rh_2(5S\text{-}MEPY)_4$ | +75 | 95 | 87 |

EXAMPLE 12

4-(N-tert-Butylazetidin-2-one)acetate by Intramolecular Carbon-Hydrogen Insertion To ethyl 3-(N-tert-butyl-N-diazoacetyl) aminopropanoate (0.111 g, 0.46 mmol) in 20 mL of anhydrous dichloromethane heated at reflux was added $Rh_2(4S\text{-}BNOX)_4$ (0.0042 g, 0.0049 mmol) all at once, and the resulting solution was refluxed for 90 min. After passing the dichloromethane solution through a plug of neutral alumina and evaporating the solvent under reduced pressure, the residue (0.064 g) was distilled (112° C. at 0.01 Torr) with a Kugelrohr apparatus to Yield 0.054 g of 85% pure product (50% yield) that gave a specific rotation of −19.4° (c=4.7 in $CHCl_3$). The following illustrates the reaction taking place.

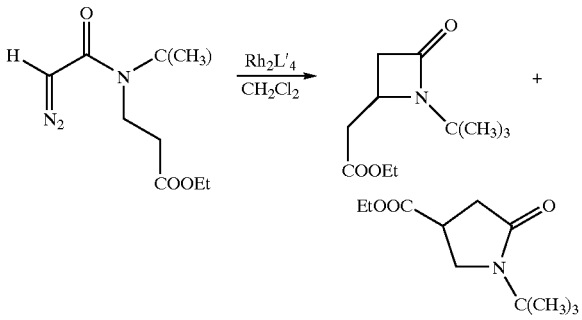

EXAMPLE 13

Preparation of 4-(2-Methyl-1-propenyl)-5,5-dimethyl-Y-butyrolactone

To 7.2 mg of $Rh_2(4S\text{-}IPOX)_4$ in 15 mL of anhydrous dichloromethane was added, by syringe pump over a 12.5 h period, 98 mg (0.50 mmol) of 2,5-dimethyl-4-hexen-2-yl diazoacetate in 5.0 mL of dichloromethane. The resulting dichloromethane solution was refluxed for 3 h, then cooled and passed through a chromatography column of neutral alumina to remove the catalyst. Evaporation of the solvent provided a residue that contained the title compound in 75% yield having an $[x]_D$ (at 22° C.) equal to +4.3° (2.2 in $CHCl_3$). The following illustrates the reaction taking place.

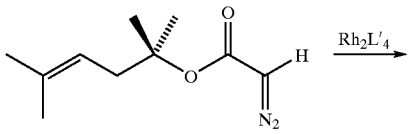

-continued

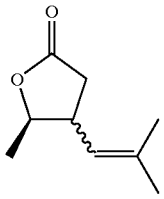

EXAMPLE 14

Nitrogen-Hydrogen Insertion By Carbenes Derived from Diazo Compounds

To a dichloromethane solution containing 1.0 mol % of $Rh_2(4R\text{-}MPOX)_4$ at room temperature will be added, dropwise by syringe pump, a dichloromethane solution of D,L-3-acetamido-3-phenyl-1-diazo-2-butanone. After addition is complete, the catalyst will be removed, the solvent evaporated, and the resulting N-acetyl-5-phenyl-2-pyrrolidone will be analyzed for optical purity.

EXAMPLE 15

Silicon-Hydrogen Insertion By Carbenes Derived from Diazo Compounds

To a dichloromethane solution containing methylphenylsilane and 1.0 mol % of $Rh_2(4S\text{-}IPOX)_4$ at room temperature will be added, dropwise by syringe pump, a dichloromethane solution, containing ethyl diazoacetate. After addition is complete, the catalyst will be removed, the solvent evaporated, and the resulting ethyl methylphenylsilylacetate will be analyzed for optical purity.

EXAMPLE 16

Addition of Silicon Hydrides to Alkenes

The addition of silicon hydrides, ranging from trialkylsilanes to trichlorosilanes, to prochiral alkenes such as -methylstyrene are performed in the presence of chiral dirhodium(ii) catalysts such as $Rh_2(4R\text{-}MPOX)_4$ (1–2 mol %) in anhydrous dichloromethane or benzene over the temperature range of 0° C. to 80° C. Following chromatographic removal of the catalyst and distillation of the solvent, the addition product or products formed by "anti-Markovnikov" addition are analyzed for asymmetric induction by standard methods.

EXAMPLE 17

Ylide Formation and Rearrangement from the Chiral Catalyst Induced Decomposition of Diazo Compounds In the Presence of Allyl Ethers Addition of ethyl diazoacetate by syringe pump to a dichloromethane solution containing cinnamyl methyl ether in the presence of 1–2 mol % of chiral dirhodium(II) catalysts such as $Rh_2(5S\text{-}MEPY)_4$ is performed at temperatures ranging from 20° C. to 40° C. Following chromatographic separation of the catalyst and distillation of the solvent, the ylide derived products formed by [2,3]-sigmatropic rearrangement is be analyzed for asymmetric induction by standard methods.

It should be noted that, although much of the discussion has involved the preferred catalysts being used in preferred reactions, this should not be seen as limiting the scope of Applicant's invention. For example, the invention includes cyclic and acyclic bridging ligands. Also, the invention includes catalysts wherein the approach to one of the metal atoms is impaired by blocking structure. Also, the reactions enantioselectively catalyzed by the catalysts of the present invention are not limited to those specific reactions described above. Certainly, all modifications which are within the ordinary skill in the art to make are considered to lie within the scope of the invention as defined by the appended claims.

I claim:

1. A method of enantioselectively inserting a carbene between a carbon and a hydrogen comprising the steps of:

providing a compound with a carbon-hydrogen bond;

providing a carbene precursor, wherein either said compound or said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexed to said second metal atom, said first bridging ligand further comprising a ring including said first complexing atom and attached to said second complexing atom, said ring also including a chiral center attached through a first bonding site to said first complexing atom, attached through a second bonding site to said ring, having a third bonding site occupied by a first substituent, and having a fourth bonding site occupied by a second substituent, and said second bridging ligand further comprising a ring including said second complexing atom and attached to said first complexing atom, said ring also including a chiral center attached through a first bonding site to said second complexing atom, attached through a second bonding site to said ring, having a third bonding site occupied by a first substituent, and having a fourth bonding site occupied by a second substituent, and wherein the R/S configuration of the chiral center on the second bridging ligand is the same as the R/S configuration of the chiral center on the first bridging ligand; and reacting said compound, said carbene precursor, and said chiral catalyst under conditions sufficient to cause said carbene insertion to proceed.

2. A method of enantioselectively inserting a carbene between a carbon and a hydrogen comprising the steps of:

providing a compound with a carbon-hydrogen bond;

providing a carbene precursor, wherein either said compound or said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexed to said second metal atom, said first bridging ligand also comprising a ring including said first complexing atom and attached to said second complexing atom, said ring also including a chiral center attached through a first bonding site to said first complexing atom, attached through a second bonding site to said ring, having a third bonding site occupied by a first substituent, and having a fourth bonding site occupied by a second substituent, and said first bridging ligand further comprising a second chiral center attached through a first bonding site to said second complexing atom, having a second bonding site occupied by a first substituent, having a third bonding site occupied by a second substituent, and having a fourth bonding site occupied by a third substituent; and reacting said compound, said carbene precursor, and said chiral catalyst under conditions sufficient to cause said carbene insertion to proceed.

3. A method of enantioselectively inserting a carbene between a carbon and a hydrogen comprising the steps of:

providing a compound with a carbon-hydrogen bond;

providing a carbene precursor, wherein either said compound or said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexed to said second metal atom, said first bridging ligand also comprising a ring including said first complexing atom and attached to said second complexing atom, said ring also including a chiral center attached through a first bonding site to said first complexing atom, attached through a second bonding site to said ring, having a third bonding site occupied by a first substituent, and having a fourth bonding site occupied by a second substituent; and blocking structure bonded to at least one of said first, second, third, and fourth bridging ligands, said blocking structure being constituted, configured, and oriented so as to substantially impair approach to the second metal atom along said axis; and reacting said compound, said carbene precursor, and said chiral catalyst under conditions sufficient to cause said carbene insertion to proceed.

4. A method of enantioselectively inserting a carbene between a carbon and a hydrogen comprising the steps of:

providing a compound with a carbon-hydrogen bond;

providing a carbene precursor, wherein either said compound or said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexed with said second metal atom, said first bridging ligand further comprising a chiral center attached through a first bonding site to the first complexing atom, and having a second bonding site occupied by a first substituent, having a third bonding site occupied by a second substituent, and having a fourth bonding site occupied by a third substituent, and said second bridging ligand further comprising a chiral center attached through a first bonding site to the second complexing atom, and having a second bonding site occupied by a first substituent, having a third bonding site occupied by a second substituent, and having a fourth bonding site occupied by a third substituent, and wherein the R/S configuration of the chiral centers on the first and second bridging ligands are all the same; and reacting said compound, said carbene precursor, and said chiral catalyst under conditions sufficient to cause said carbene insertion to proceed.

5. A method of enantioselectively inserting a carbene between a carbon and a hydrogen comprising the steps of:

providing a compound with a carbon-hydrogen bond;

providing a carbene precursor, wherein either said compound of said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexed with said second metal atom, said first bridging ligand further comprising a chiral center attached through a first bonding site to the first complexing atom, and having a second bonding site occupied by a first substituent, having a third bonding site occupied by a second substituent, and having a fourth bonding site occupied by a third substituent, and blocking structure bonded to at least one of said first, second, third, and fourth bridging ligands, said blocking structure being constituted, configured and oriented so as to substantially impair approach to the second metal atom along said axis; and reacting said compound, said carbene precursor, and said chiral catalyst under conditions sufficient to cause said carbene insertion to proceed.

6. The method of claim 1, 2, 3, 4 or 5 wherein the compound is selected from the group consisting of 3-(N-diazoacetyl)aminopropionate, 2,5-dimethyl-4-hexen-2-yl diazoacetate, N-(diazoacetylamino)acetate, n-octyl diazoacetate, and N-(1-butyl)diazoacetamide.

7. The method of claim 1, 2, 3, 4 or 5 wherein the carbene precursor is a diazo carbonyl compound.

8. The method of claim 1, 2, 3, 4 or 5 wherein the carbene precursor is a diazo compound selected from the group consisting of ethyl diazoacetate, t-butyl diazoacetate, and menthyl diazoacetate.

9. The method of claim 1, 2, 3, 4 or 5 wherein the carbene precursor is on the compound with the carbon-hydrogen bond.

10. A method of enantioselectively inserting a carbene between an oxygen and a hydrogen comprising the steps of:

providing a compound with an oxygen-hydrogen bond;

providing a carbene precursor, wherein either said compound or said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexed to said second metal atom, said first bridging ligand further comprising a ring including said first complexing atom and attached to said second complexing atom, said ring also including a chiral center attached through a first bonding site to said first complexing atom, attached through a second bonding site to said ring, having a third bonding site occupied by a first substituent, and having a fourth bonding site occupied by a second substituent, and said second bridging ligand further comprising a ring including said second complexing atom and attached to said first complexing atom, said ring also including a chiral center attached through a first bonding site to said second complexing atom, attached through a second bonding site to said ring, having a third bonding site occupied by a first substituent, and having a fourth bonding site occupied by a second substituent, and wherein the R/S configuration of the chiral center on the second bridging ligand is the same as the R/S configuration of the chiral center on the first bridging ligand; and reacting said compound, said carbene precursor, and said chiral catalyst under conditions sufficient to cause said carbene, insertion to proceed.

11. A method of enantioselectively inserting a carbene between an oxygen and a hydrogen comprising the steps of:

providing a compound with an oxygen-hydrogen bond;

providing a carbene precursor, wherein either said compound or said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexed to said second metal atom, said first bridging ligand also comprising a ring including said first complexing atom and attached to said second complexing atom, said ring also including a chiral center attached through a first bonding site to said first complexing atom, attached through a second bonding site to said ring, having a third bonding site occupied by a first substituent, and having a fourth bonding site occupied by a second substituent, and said first bridging ligand further comprising a second chiral center attached through a first bonding site to said second complexing atom, having a second bonding site occupied by a first substituent, having a third bonding site occupied by a second substituent, and having a fourth bonding site occupied by a third substituent; and reacting said compound, said carbene precursor, and said chiral catalyst under conditions sufficient to cause said carbene insertion to proceed.

12. A method of enantioselectively inserting a carbene between an oxygen and a hydrogen comprising the steps of:

providing a compound with an oxygen-hydrogen bond;

providing a carbene precursor, wherein either said compound or said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexed to said second metal atom, said first bridging ligand also comprising a ring including said first complexing atom and attached to said second complexing atom, said ring also including a chiral center attached through a first bonding site to said first complexing atom, attached through a second bonding site to said ring, having a third bonding site occupied by a first substituent, and having a fourth bonding site occupied by a second substituent; and blocking structure bonded to at least one of said first, second, third, and fourth bridging ligands, said blocking structure being constituted, configured, and oriented so as to substantially impair approach to the second metal atom along said axis; and reacting said compound, said carbene precursor, and said chiral catalyst under conditions sufficient to cause said carbene insertion to proceed.

13. A method of enantioselectively inserting a carbene between an oxygen and a hydrogen comprising the steps of:

a providing a compound with an oxygen-hydrogen bond;

providing a carbene precursor, wherein either said compound or said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexed with said second metal atom, said first bridging ligand further comprising a chiral center attached through a first bonding site to the first complexing atom, and having a second bonding site occupied by a first substituent, having a third bonding site occupied by a second substituent, and having a fourth bonding site occupied by a third substituent, and said second bridging ligand further comprising a chiral center attached through a first bonding site to the second complexing atom, and having a second bonding site occupied by a first substituent, and having a fourth bonding site occupied by second substituent, and having a fourth bonding site occupied by a third substituent, and wherein the R/S configuration of the chiral centers on the first and second bridging ligands are all the same; and reacting said compound, said carbene precursor, and said chiral catalyst under conditions sufficient to cause said carbene insertion to proceed.

14. A method of enantioselectively inserting a carbene between an oxygen and a hydrogen comprising the steps of:

providing a compound with an oxygen-hydrogen bond;

providing a carbene precursor, wherein either said compound or said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexed with said second metal atom, said first bridging ligand further comprising a chiral center attached through a first bonding site to the first complexing atom, and having a second bonding site occupied by a first substituent, having a third bonding site occupied by a second substituent, and having a fourth bonding site occupied by a third substituent, and blocking structure bonded to at least one of said first, second, third, and fourth bridging ligands, said blocking structure being constituted, configured and oriented so as to substantially impair approach to the second metal atom along said axis; and reacting said compound, said carbene precursor, and said chiral catalyst under conditions sufficient to cause said carbene insertion to proceed.

15. The method of claim 10, 11, 12, 13 or 14 wherein the compound is selected from the group consisting of cis-1,2-cyclohexanediol, 1-phenylethanol, methanol, and 2-butanol.

16. The method of claim 12, 11, 12, 13 or 14 wherein the carbene precursor is a diazo carbonyl compound.

17. The method of claim 10, 11, 12, 13 or 14 wherein the carbene precursor is a diazo compound selected from the group consisting of ethyl diazo acetate, t-butyl diazoacetate, menthyl diazoacetate, and 3-diazo-2-butanone.

18. The method of claim 10, 11, 12, 13 or 14 wherein the carbene precursor is on the compound with the oxygen-hydrogen bond.

19. A method of enantioselectively inserting a carbene between a nitrogen and a hydrogen comprising the steps of:

providing a compound with a nitrogen-hydrogen bond;

providing a carbene precursor, wherein either said compound or said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexed to said second metal atom, said first bridging ligand further comprising a ring including said first complexing atom and attached to said second complexing atom, said ring also including a chiral center attached through a first bonding site to said first complexing atom, attached through a second bonding site to said ring, having a third bonding site occupied by a first substituent, and having a fourth bonding site occupied by a second substituent, and said second bridging ligand further comprising a ring including said second complexing atom and attached to said first complexing atom, said ring also including a chiral center attached through a first bonding site to said second complexing atom, attached through a second bonding site to said ring, having a third bonding site occupied by a first substituent, and having a fourth bonding site occupied by a second substituent, and wherein the R/S configuration of the chiral center on the second bridging ligand is the same as the R/S configuration of the chiral center on the first bridging ligand; and reacting said compound, said carbene precursor, and said chiral catalyst under conditions sufficient to cause said carbene insertion to proceed.

20. A method of enantioselectively inserting a carbene between a nitrogen and a hydrogen comprising the steps of:

providing a compound with a nitrogen-hydrogen bond;

providing a carbene precursor, wherein either said compound or said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexed to said second metal atom, said first bridging ligand also comprising a ring including said first complexing atom and attached to said second complexing atom, said ring also including a chiral center attached through a first bonding site to said first complexing atom, attached through a second bonding site to said ring, having a third bonding site occupied by a first substituent, and having a fourth bonding site occupied by a second substituent, and said first bridging ligand further comprising a second chiral center attached through a first bonding site to said second complexing atom, having a second bonding site occupied by a first substituent, having a third bonding site occupied by a second substituent, and having a fourth bonding site occupied by a third substituent; and reacting said compound, said carbene precursor, and said chiral catalyst under conditions sufficient to cause said carbene insertion to proceed.

21. A method of enantioselectively inserting a carbene between a nitrogen and a hydrogen comprising the steps of:

providing a compound with a nitrogen-hydrogen bond;

providing a carbene precursor, wherein either said compound or said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexed to said second metal atom, said first bridging ligand also comprising a ring including said first complexing atom and attached to said second complexing atom, said ring also including a chiral center attached through a first bonding site to said first complexing atom, attached through a second bonding site to said ring, having a third bonding site occupied by a first substituent, and having a fourth bonding site occupied by a second substituent; and blocking structure bonded to at least one of said first, second, third, and fourth bridging ligands, said blocking structure being constituted, configured, and oriented so as to substantially impair approach to the second metal atom along said axis; and reacting said compound, said carbene precursor, and said chiral catalyst under conditions sufficient to cause said carbene insertion to proceed.

22. A method of enantioselectively inserting a carbene between a nitrogen and a hydrogen comprising the steps of:

providing a compound with a nitrogen-hydrogen bond;

providing a carbene precursor, wherein either said compound or said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexed with said second metal atom, said first bridging ligand further comprising a chiral center attached through a first bonding site to the first complexing atom, and having a third bonding site occupied by a first substituent having a third bonding site occupied by a second substituent, and having a fourth bonding site occupied by a third substituent, and said second bridging ligand further comprising a chiral center attached through a first bonding site to the second complexing atom, and having a second bonding site occupied by a first substituent, having a third bonding site occupied by a second substituent, and having a fourth bonding site occupied by a third substituent, and wherein the R/S configuration of the chiral centers on the first and second bridging ligands are all the same; and reacting said compound, said carbene precursor, and said chiral catalyst under conditions sufficient to cause said carbene insertion to proceed.

23. A method of enantioselectively inserting a carbene between a nitrogen and a hydrogen comprising the steps of:

providing a compound with a nitrogen-hydrogen bond;

providing a carbene precursor, wherein either said compound or said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexed with said second metal atom, said first bridging ligand further comprising a chiral center attached through a first bonding site to the first complexing atom, and having a second bonding site occupied by a first substituent, having a third bonding site occupied by a second substituent, and having a fourth bonding site occupied by a third substituent, and blocking structure bonded to at least one of said first, second, third, and fourth bridging ligands, said blocking structure being constituted, configured and oriented so as to substantially impair approach to the second metal atom along said axis; and reacting said compound, said carbene precursor, and said chiral catalyst under conditions sufficient to cause said carbene insertion to proceed.

24. The method of claim 19, 20, 21, 22 or 23 wherein the compound is selected from the group consisting of N-(1-phenylethyl)acetamide, N-(2-butyl)acetamide, and 3-acetyl-B*-lactam.

25. The method of claim 19, 20, 21, 22, or 23 wherein the carbene precursor is a diazo carbonyl compound.

26. The method of claim 19, 20, 21, 22 or 23 wherein the carbene precursor is a diazo compound selected from the group consisting of ethyl diazo acetate, t-butyl diazoacetate, methyl diazoacetate, and 3-diazo-2-butanone.

27. The method of claim 19, 20, 21, 22 or 23 wherein the carbene precursor is on the compound with the nitrogen-hydrogen bond.

28. A method of enantioselectively inserting a carbene between a silicon and a hydrogen comprising the steps of:

providing a compound with a silicon-hydrogen bond;

providing a carbene precursor, wherein either said compound or said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexed to said second metal atom, said first bridging ligand further comprising a ring including said first complexing atom and attached to said second complexing atom, said ring also including a chiral center attached through a first bonding site to said first complexing atom, attached through a second bonding site to said ring, having a third bonding site occupied by a first substituent, and having a fourth bonding site occupied by a second substituent, and said second bridging ligand further comprising a ring including said second complexing atom and attached to said first complexing atom, said ring also including a chiral center attached through a first bonding site to said second complexing atom, attached through a second bonding site to said ring, having a third bonding site occupied by a first substituent, and having a fourth bonding site occupied by a second substituent, and wherein the R/S configuration of the chiral center on the second bridging ligand is the same as the R/S configuration of the chiral center on the first bridging ligand; and reacting said compound, said carbene precursor, and said chiral catalyst under conditions sufficient to cause said carbene insertion to proceed.

29. A method of enantioselectively inserting a carbene between a silicon and a hydrogen comprising the steps of:

providing a compound with a silicon-hydrogen bond;

providing a carbene precursor, wherein either said compound or said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexed to said second metal atom, said first bridging ligand also comprising a ring including said first complexing atom and attached to said second complexing atom, said ring also including a chiral center attached through a first bonding site to said first complexing atom, attached through a second bonding site to said ring, having a third bonding site occupied by a first substituent, and having a fourth bonding site occupied by a second substituent, and said first bridging ligand further comprising a second chiral center attached through a first bonding site to said second complexing atom, having a second bonding site occupied by a first substituent, having a third bonding site occupied by a second substituent, and having a fourth bonding site occupied by a third substituent; and reacting said compound, said carbene precursor, and said chiral catalyst under conditions sufficient to said carbene insertion to proceed.

30. A method of enantioselectively inserting a carbene between a silicon and a hydrogen comprising the steps of:

providing a compound with a silicon-hydrogen bond;

providing a carbene precursor, wherein either said compound or said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexing to said second metal atom, said first bridging ligand also comprising a ring including said first complexing atom and attached to said second complexing atom, said ring also including a chiral center attached through a first bonding site to said first complexing atom, attached through a second bonding site to said ring, having a third bonding site occupied by a first substituent, and having a fourth bonding site occupied by a second substituent; and blocking structure bonded to at least one of said first, second, third, and fourth bridging ligands, said blocking structure being constituted, configured, and oriented so as to substantially impair approach to the second metal atom along said axis; and reacting said compound, said carbene precursor, and said chiral catalyst under conditions sufficient to cause said carbene insertion to proceed.

31. A method of enantioselectively inserting a carbene between a silicon and a hydrogen comprising the steps of:

providing a compound with a silicon-hydrogen bond;

providing a carbene precursor, wherein either said compound or said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexed with said second metal atom, said first bridging ligand further comprising a chiral center attached through a first bonding site to the first complexing atom, and having a second bonding site occupied by a first substituent, having a third bonding site occupied by a second substituent, and having a fourth bonding site occupied by a third substituent, and said second bridging ligand further comprising a chiral center attached through a first bonding site to the second complexing atom, and having a second bonding site occupied by a first substituent, having a third bonding site occupied by a second substituent, and having a fourth bonding site occupied by a third substituent, and wherein the R/S configuration of the chiral centers on the first and second bridging ligands are all the same; and reacting said compound, said carbene precursor, and said chiral catalyst under conditions sufficient to cause said carbene insertion to proceed.

32. A method of enantioselectively inserting a carbene between a silicon and a hydrogen comprising the steps of:

providing a compound with a silicon-hydrogen bond;

providing a carbene precursor, wherein either said compound or said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexed with said second metal atom, said first bridging ligand further comprising a chiral center attached through a first bonding site to the first complexing atom, and having a second bonding site occupied by a first substituent, having a third bonding site occupied by a second substituent, and having a fourth bonding site occupied by a third substituent, and blocking structure bonded to at least one of said first, second, third, and fourth bridging ligands, said blocking structure being constituted, configured and oriented so as to substantially impair approach to the second metal atom along said axis; and reacting said compound, said carbene precursor, and said chiral catalyst under conditions sufficient to cause said carbene insertion to proceed.

33. The method of claim 28, 29, 30, 31 or 32 wherein the carbene precursor is a diazo carbonyl compound.

34. The method of claim 28, 29, 30, 31 or 32 wherein the carbene precursor is a diazo compound selected from the group consisting of ethyl diazo acetate, t-butyl diazoacetate, methyl diazoacetate, and 3-diazo-2-butanone.

35. The method of claim 28, 29, 30, 31 or 32 wherein the carbene precursor is on the compound with the silicon-hydrogen bond.

36. A method of enantioselectively inserting a carbene between a sulfur and a hydrogen comprising the steps of:

providing a compound with a sulfur-hydrogen bond;

providing a carbene precursor, wherein either said compound or said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexed to said second metal atom, said first bridging ligand further comprising a ring including said first complexing atom and attached to said second complexing atom, said rig also including a chiral center attached through a first bonding site to said first complexing atom, attached through a second bonding site to said ring, having a third bonding site occupied by a first substituent, and having a fourth bonding site occupied by a second substituent, and said second bridging ligand further comprising a ring including said second complexing atom and attached to said first complexing atom, said ring also including a chiral center attached through a first bonding site to said second complexing atom, attached through a second bonding site to said ring, having a third bonding site occupied by a first substituent, and having a fourth bonding site occupied by a second substituent, and wherein the R/S configuration of the chiral center on the second bridging ligand is the same as the R/S configuration of the chiral center on the first bridging ligand; and reacting said compound, said carbene precursor, and said chiral catalyst under conditions sufficient to cause said carbene insertion to proceed.

37. A method of enantioselectively inserting a carbene between a sulfur and a hydrogen comprising the steps of:

providing a compound with a sulfur-hydrogen bond;

providing a carbene precursor, wherein either said compound or said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexed to said second metal atom, said first bridging ligand also comprising a ring including said first complexing atom and attached to said second complexing atom, said ring also including a chiral center attached through a first bonding site to said first complexing atom, attached through a second bonding site to said ring, having a third bonding site occupied by a first substituent, and having a fourth bonding site occupied by a second substituent, and said first bridging ligand further comprising a second chiral center attached through a first bonding site to said second complexing atom, having a second bonding site occupied by a first substituent, having a third bonding site occupied by a second substituent, and having a fourth bonding site occupied by a third substituent; and reacting said compound, said carbene precursor, and said chiral catalyst under conditions sufficient to cause said carbene insertion to proceed.

38. A method of enantioselectively inserting a carbene between a sulfur and a hydrogen comprising the steps of:

providing a compound with a sulfur-hydrogen bond;

providing a carbene precursor, wherein either said compound or said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexed to said second metal atom, said first bridging ligand also comprising a ring including said first complexing atom and attached to said second complexing atom, said ring also including a chiral center attached through a first bonding site to said first complexing atom, attached through a second bonding site to said ring, having a third bonding site occupied by a first substituent, and having a fourth bonding site occupied by a second substituent; and blocking structure bonded to at least one of said first, second, third, and fourth bridging ligands, said blocking structure being constituted, configured, and oriented so as to substantially impair approach to the second metal atom along said axis; and reacting said compound, said carbene precursor, and said chiral catalyst under conditions sufficient to cause said carbene insertion to proceed.

39. A method of enantioselectively inserting a carbene between a sulfur and a hydrogen comprising the steps of:

providing a compound with a sulfur-hydrogen bond;

providing a carbene precursor, wherein either said compound or said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexed with said second metal atom, said first bridging ligand further comprising a chiral center attached through a first bonding site to the first complexing atom, sand having a second bonding site occupied by a first substituent, having a third bonding site occupied by a second substituent, and having a fourth bonding site occupied by a third substituent, and said second bridging ligand further comprising a chiral center attached through a first bonding site to the second complexing atom, and having a second bonding site occupied by a first substituent, having a third bonding site occupied by a second substituent, and having a fourth bonding site occupied by a third substituent, and wherein the R/S configuration of the chiral centers on the first and second bridging ligands are all the same; and reacting said compound, said carbene precursor, and said chiral catalyst under conditions sufficient to cause said carbene insertion to proceed.

40. A method of enantioselectively inserting a carbene between a sulfur and a hydrogen comprising the steps of:

providing a compound with a sulfur-hydrogen bond;

providing a carbene precursor, wherein either said compound or said carbene precursor is prochiral;

providing a chiral catalyst comprising a nucleus with a first and second atom of the same metal aligned on an axis, said metal selected from the group consisting of rhodium, ruthenium, chromium, molybdenum, tungsten, rhenium and osmium; and first, second, third and fourth bridging ligands oriented radially to the axis, each ligand having a first and second complexing atom, the first complexing atom of each of said bridging ligands being complexed with said first metal atom, and the second complexing atom of each of said bridging ligands being complexed with said second metal atom, said first bridging ligand further comprising a chiral center attached through a first bonding site to the first complexing atom, and having a second bonding site occupied by a first substituent, having a third bonding site occupied by a second substituent, and having a fourth bonding site occupied by a third substituent, and blocking structure bonded to at least one of said first, second, third, and fourth bridging ligands, said blocking structure being constituted, configured and oriented so as to substantially impair approach to the second metal atom along said axis; and reacting said compound, said carbene precursor, and said chiral catalyst under conditions sufficient to cause said carbene insertion to proceed.

41. The method of claim 36, 37, 38, 39 or 40 wherein the carbene precursor is a diazo carbonyl compound.

42. The method of claim 36, 37, 38, 39 or 40 wherein the carbene precursor is a diazo compound, selected from the group consisting of ethyl diazo acetate, t-butyl diazoacetate, methyl diazoacetate, and 3-diazo-2-butanone.

43. The method of claim 36, 37, 38, 39 or 40 wherein the carbene precursor is on the compound with the sulfur-hydrogen bond.

44. The method of claims 1, 10, 19, 28 or 36 wherein one and only one of the first and second substituents on the chiral center of the first bridging ligand is a first carboxylate group attached to the chiral center by the carbonyl carbon, and wherein one and only one of the first and second substituents on the chiral center of the second bridging ligand is a second carboxylate group attached to the chiral center by the carbonyl carbon.

45. The method of claim 44 wherein the first and second carboxylate groups are independently selected from the group consisting of methyl carboxylate and isopropyl carboxylate.

46. The method of claims 2, 11, 20, 29 or 37 wherein one and only one of the first and second substituents on the first chiral center of the first bridging ligand is a first carboxylate group attached to the first chiral center by the carbonyl carbon, and wherein one and only one of the first and second substituents on the second chiral center of the first bridging ligand is a second carboxylate group attached to the second chiral center by the carbonyl carbon.

47. The method of claim 46 wherein the first and second carboxylate groups are independently selected from the group consisting of methyl carboxylate and isopropyl carboxylate.

48. The method of claims 3, 12, 21, 30 or 38 wherein one and only one of the first and second substituents on the chiral center of the first bridging ligand is a carboxylate group attached to the chiral center by the carbonyl carbon.

49. The method of claim 48 wherein the carboxylate group is selected from the group consisting of methyl carboxylate and isopropyl carboxylate.

50. The method of claim 4, 13, 22, 31 or 39 wherein one or two, but not three, of the first, second and third substituents on the chiral center of the first bridging ligand is a first carboxylate group attached to the chiral center by the carbonyl carbon, and wherein one or two, but not three, of the first, second and third substituents on the chiral center of the second bridging ligand is a second carboxylate group attached to the chiral center by the carbonyl carbon.

51. The method of claim 50 wherein the first and second carboxylate groups are independently selected from the group consisting of methyl carboxylate and isopropyl carboxylate.

52. The method of claims 5, 14, 23 32, or 40 wherein one or tow, but not three, of the first, second and third substituents on the chiral center of the first bridging ligand is a carboxylate group attached to the chiral center by the carbonyl carbon.

53. The method of claim 52 wherein the carboxylate group is selected from the group consisting of methyl carboxylate and isopropyl carboxylate.

*54. A method of enantioselectively catalyzing a reaction comprising the steps of:*

*providing a prochiral compound,*

*providing a chiral catalyst comprising*

*a nucleus with a first and second atom of the same metal aligned on an axis, said metal selected from the group consisting of rhodium, ruthenium, chromium, molybdenum, tungsten, rhenium and osmium; and*

*first, second, third and fourth bridging ligands oriented radially to the axis,*

*each ligand having a first and second complexing atom, the first complexing atom of each of said bridging ligands being complexed with said first metal atom, and the second complexing atom of each of said bridging ligands being complexed to said second metal atom,*

*said first bridging ligand further comprising a ring including said first complexing atom and attached to said second complexing atom, said ring also including a chiral center attached through a first bonding site to said first complexing atom, attached through a second bonding site to said ring, having a third bonding site occupied by a first substituent, and having a fourth bonding site occupied by a second substituent, and*

*said second bridging ligand further comprising a ring including said second complexing atom and attached to said first complexing atom, said ring also including a chiral center attached through a first bonding site to said second complexing atom, attached through a second bonding site to said ring, having a third bonding site occupied by a first substituent, and having a fourth bonding site occupied by a second substituent, and wherein the R/S configuration of the chiral center on the second bridging ligand is the same as the R/S configuration of the chiral center on the first bridging ligand; and*

*reacting said prochiral compound and said chiral catalyst under conditions sufficient cause the reaction.*

*55. The method of claim 54 wherein said third bridging ligand further comprises a ring including said first complexing atom and attached to said second complexing atom, said ring also including a chiral center attached through a first bonding site to said first complexing atom, attached through a second bonding site to said ring, having a third bonding site occupied by a first substituent, and having a fourth bonding site occupied by hydrogen, and wherein the R/S configuration of the chiral center on the third bridging ligand is the same as the R/S configuration of the chiral center on the first bridging ligand.*

*56. The method of claim 55 wherein said fourth bridging ligand further comprising a ring including said second complexing atom and attached to said first complexing atom, said ring also including a chiral center attached through a first bonding site to said second complexing atom, attached through a second bonding site to said ring, having a third bonding site occupied by a first substituent, and having a fourth bonding site occupied by hydrogen, and wherein the R/S configuration of the chiral center on the fourth bridging ligand is the same as the R/S configuration of the chiral center on the first bridging ligand.*

*57. The method of claim 54 wherein the bridging ligands with a chiral center are selected from the group consisting of: Oxazolidinones, Pyrrolidinones, *B-lactams, *Y-lactams, *S-lactams, and their analogs wherein S replaces O as the complexing atom.*

*58. The method of claim 54 wherein the bridging ligands with a chiral center are selected from the group consisting of: (4S) isopropyl oxazolidinone, (4S) benzyl oxazolidinone, (4S) methyl oxazolidinone, (5S) methyl 2-pyrrolidinone-5-carboxylate, (5S) isopropyl 2-pyrrolidinone-5-carboxylate.*

*59. A method of enantioselectively catalyzing a reaction comprising the steps of:*

*providing a prochiral compound,*

*providing a chiral catalyst comprising*

*a nucleus with a first and second atom of the same metal aligned on an axis, said metal selected from the group consisting of rhodium, ruthenium, chromium, molybdenum, tungsten, rhenium and osmium; and*

*first, second, third and fourth bridging ligands oriented radially to the axis,*

*each ligand having a first and second complexing atom, the first complexing atom of each of said bridging ligands being complexed with said first metal atom, and the second complexing atom of each of said bridging ligands being complexed with said second metal atom,*

*said first bridging ligand further comprising a chiral center attached through a first bonding site to the first complexing atom, and having a second bonding site occupied by a first substituent, having a third bonding site occupied by a second substituent, and having a fourth bonding site occupied by a third substituent, and*

*said second bridging ligand further comprising a chiral center attached through a first bonding site to the second complexing atom, and having a second bonding site occupied by a first substituent, having a third bonding site occupied by a second substituent, and having a fourth bonding site occupied by a third substituent, and*

*wherein the R/S configuration of the chiral centers on the first and second bridging ligands are all the same; and*

*reacting said prochiral compound and said chiral catalyst under conditions sufficient cause the reaction.*

*60. The method of claim 54 or 59 wherein the first and second bridging ligand are radially adjacent.*

*61. The method of claim 54 or 59 wherein the first and second bridging ligand are radially opposite.*

*62. The method of claim 54 or 59 wherein one and only one of the first and second substituents on the chiral center of the first bridging ligand is a first carboxylate group attached to the chiral center by the carbonyl carbon, and wherein one and only one of the first and second substituents on the chiral center of the second bridging ligand is a second carboxylate group attached to the chiral center by the carbonyl carbon.*

*63. The method of claim 62 wherein the first and second carboxylate groups are independently selected from the group consisting of methyl carboxylate and isopropyl carboxylate.*

*64. A method of enantioselectively catalyzing a reaction comprising the steps of:*

*providing a prochiral compound,*

*providing a chiral catalyst comprising*

*a nucleus with a first and second atom of the same metal aligned on an axis, said metal selected from the group consisting of rhodium, ruthenium, chromium, molybdenum, tungsten, rhenium and osmium; and*

*first, second, third and fourth bridging ligands oriented radially to the axis,*

*each ligand having a first and second complexing atom, the first complexing atom of each of said bridging ligands being complexed with said first metal atom, and the second complexing atom of each of said bridging ligands being complexed to said second metal atom,*

*said first bridging ligand also comprising a ring including said first complexing atom and attached to said second complexing atom, said ring also including a chiral center attached through a first bonding site to said first complexing atom, attached through a second bonding site to said ring, having a third bonding site occupied by a first substituent, and having a fourth bonding site occupied by a second substituent, and*

*said first bridging ligand further comprising a second chiral center attached through a first bonding site to said second complexing atom, having a second bonding site occupied by a first substituent, having a third bonding site occupied by a second substituent, and having a fourth bonding site occupied by a third substituent; and*

*reacting said prochiral compound and said chiral catalyst under conditions sufficient cause the reaction.*

*65. A method of enantioselectively catalyzing a reaction comprising the steps of:*

*providing a prochiral compound,*

*providing a chiral catalyst comprising*

*a nucleus with a first and second atom of the same metal aligned on an axis, said metal selected from the group consisting of rhodium, ruthenium, chromium, molybdenum, tungsten, rhenium and osmium; and*

*first, second, third and fourth bridging ligands oriented radially to the axis,*

*each ligand having a first and second complexing atom, the first complexing atom of each of said bridging ligands being complexed with said first metal atom, and the second complexing atom of each of said bridging ligands being complexed to said second metal atom,*

*said first bridging ligand also comprising a ring including said first complexing atom and attached to said second complexing atom, said ring also including a chiral center attached through a first bonding site to said first complexing atom, attached through a second bonding site to said ring, having a third bonding site occupied by a first substituent, and having a fourth bonding site occupied by a second substituent; and*

*blocking structure bonded to at least one of said first, second, third, and fourth bridging ligands, said blocking structure being constituted, configured, and oriented so as to substantially impair approach to the second metal atom along said axis; and*

*reacting said prochiral compound and said chiral catalyst under conditions sufficient cause the reaction.*

*66. A method of enantioselectively catalyzing a reaction comprising the steps of:*

*providing a prochiral compound,*

*providing a chiral catalyst comprising*

*a nucleus with a first and second atom of the same metal aligned on an axis, said metal selected from the group consisting of rhodium, ruthenium, chromium, molybdenum, tungsten, rhenium and osmium; and*

*first, second, third and fourth bridging ligands oriented radially to the axis,*

*each ligand having a first and second complexing atom, the first complexing atom of each of said bridging ligands being complexed with said first metal atom, and the second complexing atom of each of said bridging ligands being complexed with said second metal atom,*

*said first bridging ligand further comprising a chiral center attached through a first bonding site to the first complexing atom, and having a second bonding site occupied by a first substituent, having a third bonding site occupied by a second substituent, and having a fourth bonding site occupied by a third substituent, and*

*blocking structure bonded to at least one of said first, second, third, and fourth bridging ligands, said blocking structure being constituted, configured and oriented so as to substantially impair approach to the second metal atom along said axis; and*

*reacting said prochiral compound and said chiral catalyst under conditions sufficient cause the reaction.*

*67. The method of claim 54, 59, 64, 65, or 66 wherein one of the substituents on the first bridging ligand is hydrogen.*

*68. The method of claim 54, 59, 64, 65 or 66 wherein said first, second, third, and fourth bridging ligands are all the same.*

*69. The method of claim 54, 59, 64, 65 or 66 wherein the complexing atom to which the chiral centers are bonded is nitrogen.*

*70. The method of claim 54, 59, 64, 65 or 66 wherein the ratio of the volume of the first substituents to the volume of the second substituents on each of the chiral centers is less than about 0.8.*

*71. The method of claim 54, 59, 64, 65 or 66 wherein the ratio of the volume of the first substituents to the volume of the second substituents on each of the chiral centers is less than about 0.5*

* * * * *